(12) United States Patent
Smith

(10) Patent No.: US 12,080,406 B2
(45) Date of Patent: *Sep. 3, 2024

(54) TRACKING AND QUALITY ASSURANCE OF PATHOLOGY, RADIOLOGY AND OTHER MEDICAL OR SURGICAL PROCEDURES

(71) Applicant: Complete Consent, LLC, Savannah, GA (US)

(72) Inventor: Sidney P. Smith, Savannah, GA (US)

(73) Assignee: COMPLETE CONSENT, LLC, Savannah, GA (US)

( * ) Notice: Subject to any disclaimer, the term of this patent is extended or adjusted under 35 U.S.C. 154(b) by 510 days.

This patent is subject to a terminal disclaimer.

(21) Appl. No.: 16/923,883

(22) Filed: Jul. 8, 2020

(65) Prior Publication Data

US 2020/0342984 A1 Oct. 29, 2020

Related U.S. Application Data

(63) Continuation-in-part of application No. 16/853,638, filed on Apr. 20, 2020, now Pat. No. 11,881,303, which is a continuation-in-part of application No. 14/188,271, filed on Feb. 24, 2014, now abandoned.

(60) Provisional application No. 61/768,612, filed on Feb. 25, 2013.

(51) Int. Cl.
*G16H 40/20* (2018.01)
(52) U.S. Cl.
CPC .................. *G16H 40/20* (2018.01)
(58) Field of Classification Search
CPC .................. G16H 40/20; G16H 10/40
See application file for complete search history.

(56) References Cited

U.S. PATENT DOCUMENTS

| | | | |
|---|---|---|---|
| 8,165,363 B2 | 4/2012 | Soenksen et al. | |
| 8,571,286 B2 | 10/2013 | Soenksen et al. | |
| 2002/0164810 A1* | 11/2002 | Dukor | G01N 33/57415 436/171 |
| 2004/0030584 A1 | 2/2004 | Harris | |
| 2004/0138920 A1 | 7/2004 | Sawanaga | |
| 2005/0091084 A1* | 4/2005 | McGuigan | G16H 20/10 705/3 |
| 2008/0051679 A1 | 2/2008 | Maljanian | |
| 2008/0077019 A1* | 3/2008 | Xiao | G06T 7/0012 600/474 |
| 2011/0215930 A1* | 9/2011 | Lee | A61B 5/0077 382/128 |

(Continued)

OTHER PUBLICATIONS

Admin (Select the Appropriate Inhalation Treatment code, Published on Apr. 6, 2010).

*Primary Examiner* — Reginald R Reyes
(74) *Attorney, Agent, or Firm* — Nixon & Vanderhye, PC

(57) ABSTRACT

Described systems and techniques provide for tracking respective medical events such as a patient's pathology specimen etc., based on a unique medical event tracking number throughout the diagnosis and treatment associated with that specimen. The system and technique generation of living reports of patient health conditions that enables medical event-based tracking in a manner that substantially improves medical care by facilitating "closing-the-loop" between the many medical service providers and the laboratories that may be involved in a particular diagnosis and treatment.

20 Claims, 16 Drawing Sheets

(56) References Cited

U.S. PATENT DOCUMENTS

2012/0158633 A1  6/2012  Eder
2014/0117080 A1  5/2014  Schwarz

* cited by examiner

FIGURE 3

| Procedure Recommended Code 24 | Quality Assurance Module Coding System 22 | | ICD-10 CODE DIAGNOSIS 23 | |
|---|---|---|---|---|
| | Time Interval 25 | | | Referral Code 26 |
| | 0, 0, 0, 0 | | 0, 0, 0, 0 | |
| | Numerical | Interval | | Surgeon |
| Pathology Codes | 0 | 0 | 1. | Oncologist |
| 1. Follow-up Examination | 1 | Day | 2. | Radiologist |
| 2. Biopsy | 2 | Week | 3. | Neurologist |
| 3. Excision | 3 | Month | 4. | Other |
| 4. Excision with Margins | 4 | Year | 5. | |
| 5. Send Specimen to Referral Pathologist | | | | |
| 6. Other | | | | |
| 7. ETC | | | | |
| Radiology Codes | | | | |
| 1. Repeat Procedure | | | | |
| 2. Plain Films | | | | |
| 3. CT | | | | |
| 4. MRI | | | | |
| 5. Mammogram | | | | |
| 6. Ultrasound | | | | |
| 7. Biopsy | | | | |
| 8. Other | | | | |

Example Default Codes 27

Melanoma – Recommend Annual follow-ups 172.2

01.14 / 08.00

Breast Lesion – Recommended
Six (6) Month Follow-up Mammogram 01.63 / 08.00

QAM

TRACKING AND QUALITY ASSURANCE OF PATHOLOGY, RADIOLOGY AND OTHER MEDICAL OR SURGICAL PROCEDURES

CROSS-REFERENCES TO RELATED APPLICATIONS

This application is a continuation-in-part of U.S. patent application Ser. No. 16/853,638, filed Feb. 20, 2020, which is a continuation-in-part of U.S. patent application Ser. No. 14/188,271, filed Feb. 24, 2014, which claims the benefit of U.S. Provisional Patent Application Ser. No. 61/768,612, filed Feb. 25, 2013. The entire contents of U.S. patent application Ser. No. 14/188,271 and U.S. Provisional Patent Application Ser. No. 61/768,612 are herein incorporated by reference.

STATEMENT REGARDING FEDERALLY SPONSORED RESEARCH OR DEVELOPMENT (NOT APPLICABLE)

BACKGROUND

When patients present to their physician with a possible melanoma, the physician evaluates the concerning area and performs a biopsy. The biopsy is sent to a lab which, in turn, renders a diagnosis, and the patient is contacted and treated. The biopsy diagnosis is interpreted by a physician or pathologist, who may either render a final diagnosis regarding the suspected melanoma, make further referrals to other specialists, or recommend additional tests. A key to successful diagnosis and/or treatment of the patient's condition is the ability to complete each of the steps in this process of referrals and testing. At present, it is estimated that a substantial percentage of diagnoses and/or treatments, are unsuccessful and several billion dollars are spent on malpractice claims due to incomplete steps in various treatment plans. A common cause of diagnostic error is failure to respond to medical data in an appropriate manner, often referred to as failing to "close the loop".

Medical computer systems in prevalent use today merely digitize the previous pre-digital filing systems in medical offices and hospitals. The current electronic health record (EHR) systems are designed to store medical data linked to a patient's name and date of birth, as was the case with paper charts before the digital age.

The purpose of an EHR system is to document patient care and store patient medical files. Records are saved in electronic files linked to patients' unique identifying information, such as their date of birth, social security number, unique medical record number, and/or address. This unique identifying information is called Personal Medical Information (PMI). Attaching the patient's unique identifying information to medical events such as a lab or pathology report enables the EHR software to file information into the patient's chart. This type of storage is identical to the method used in paper charts prior to the creation of EHR.

The technical name for these EHR files is a portable document format (PDF) file. The PDF files are stored using a common EHR software language called Health Language 7 (HL7). All EHRs use HL7 software. However, the EHR vendors file the patient's medical information in different ways, which means EHRs cannot efficiently send files between vendors. This results in a lack of interoperability.

EHR software currently in widespread use, arranges data with each patient having a unique file with sub-files for different aspects, such as, for example, labs, imaging, pathology results, and physicians' notes. At present, patients have access to their files through patient portals for every physician and hospital where they have received treatment. Enabling patients' access to their medical records via patient portals is an advancement created by EHRs. The EHR record sequentially stacks PDF files linked to PMI. Other than linking to PMI, PDF files have no digital relationship and are fixed in time. Due to PDF's static and limited data connectivity, significant advances of interoperability are impossible. Benefits that have been achieved through creation of the EHR HL7 PDF storage software include shared and quick access to a patient's records and the automatic return of lab and imaging results. Other benefits include the ability for multiple users to use charts simultaneously, electronic prescribing, integrated physician dispensing, checking of drug-drug interactions and medication allergies, recovery of files after disasters, spell checking, and improved legibility.

While these benefits are substantial, several of the most important goals that prompted the development of EHR are not being satisfactorily achieved: interoperability, collaborative quality care, effective communication, and dynamic patient-centric medical records.

At a high level, the solution to attaining interoperability, quality care, communication, and dynamic medical records would be creating a single large electronic storage system, or health information exchange (HIE) linked to PMI. Use of HIE would provide every patient with a single portal to which every physician and health system would send patient information. Creating HIEs has been a challenge due to resistance from EHR vendors and large heath care systems. Medical data is a commodity and a competitive advantage for EHR companies and health systems. However, sharing medical information between EHR vendors and health systems is typically not in their financial interest. Using PMI as a key to medical record storage with the HL7 language, EHR systems cannot efficiently create interoperability, shared quality metrics, communication, and a dynamic medical record.

Thus, further solutions are desired for interoperability of medical record systems in order to achieve improved efficiency and accuracy of treatment.

SUMMARY OF EXAMPLE EMBODIMENTS

Example embodiments provide solutions to move from PMI-based electronic health records to a new concept based on tracking medical events with tracking numbers. These embodiments solve vexing problems in medicine interoperability, shared quality care, communication, and create a dynamic medical record.

The described embodiments relate to automated tracking and quality control electronic health records for pathology, surgery, and medical treatment not linked to PMI but uniquely linked to medical event tracking. The system automates the entire process, adds time metrics to improve patient safety, and coordinates all involved parties.

A process and a platform are described which enable physicians to communicate recommendations and referrals with time metrics accessible to all health care partners. Through point of origin tracking numbers for specimens/labs/imaging studies integrated with the lab, imaging center, and referrals, and stored in the Quality Assurance Module all parties are effectively informed of each step of the process, and share safeguards to make sure all recommendations or referrals are completed. The process and platform may be used in any medical fields. In each field of medicine such as pathology, surgery, and radiology, etc., it is desirable to follow diagnosis, recommendations, and patients' follow up. The physician, surgeon, pathologist, and patients all need a mechanism to consistently follow labs, specimens (including x-ray reports), or recommendations to demonstrate appropriate care is received.

Medical event tracking and quality assurance systems described provide a quality assurance module that interfaces between patient information systems (e.g. Electronic Health Record systems (EHR)) lab information systems (LIS) and Radiology Picture Archiving and Communication System (PACS). The system and techniques provide for tracking respective medical events such as a patient's pathology specimen, x-ray image, referral etc., based on a unique medical event tracking number throughout the diagnosis and treatment associated with that specimen, image, or lab. The system and technique enable medical tracking in a manner that substantially improves medical care by facilitating "closing-the-loop" between the many medical service providers, the laboratories/imaging centers that may be involved in a particular diagnosis and treatment.

In an exemplary embodiment, a medical event tracking computer system comprises: a memory configured to store a plurality of tracked medical event records, each tracked medical event record including a unique medical event tracking number corresponding to a tracked medical event in relation to a patient; at least one network communication interface; and a processing system comprising at least one processor. The processing system is configured to provide, via at least one network communication interface, a first application programming interface to a patient information system and a second application programming interface to a medical testing information system.

In response to a first type of message from the patient information system received via the first application programming interface, the processing system: (1) generates a unique medical event tracking number, (2) generates a corresponding tracked medical event record in at least one memory, and (3) associates at least one timer with the generated tracked medical event record. An event type and/or event subtype and the associated timer of the generated tracked medical event record is set in accordance with a code included in the received first type of message. In response to a second type of message from the medical testing information system received via the second application programming interface, the processing system: (1) updates a status of the generated tracked medical event record, and (2) transmits a status message to the patient information system. The processing system also transmits one or more messages including information associated with the generated tracked medical event record to a requester.

In another example embodiment, a computer-implemented medical event tracking method comprises: providing, via at least one network communication interface, a first application programming interface to a patient information system and a second application programming interface to a medical testing information system. In response to a first type of message received from the patient information system via the first application programming interface: (1) generates a unique medical event tracking number, the method (2) generates a corresponding tracked medical event record in the at least one memory, and (3) associates at least one timer with the generated tracked medical event record, wherein an event type and/or event subtype and the associated timer of the generated tracked medical event record is set in accordance with a code included in the received first type of message. In response to a second type of message received from the medical testing information system via the second application programming interface, the method: (1) updates a status of the generated tracked medical event record, and (2) transmits a status message to the patient information system. The method also transmits one or more messages including information associated with the generated tracked medical event record to a requester.

In another example embodiment, a medical event tracking is provided. The instructions, when executed by a processing system including one or more processors, causes the processing system to perform operations providing, via at least one network communication interface, a first application programming interface to a patient information system and a second application programming interface to a medical testing information system.

In response to a first type of message received from the patient information system via the first application programming interface, the processing system is caused to: (1) generate a unique medical event tracking number, (2) generate a corresponding tracked medical event record in the at least one memory, and (3) associate at least one timer with the generated tracked medical event record, wherein an event type and/or event subtype and the associated timer of the generated tracked medical event record is set in accordance with a code included in the received first type of message. In response to a second type of message received from the medical testing information system via the second application programming interface, the processing system is caused to: (1) update a status of the generated tracked medical event record, and (2) transmit a status message to the patient information system. The processing system is also caused to transmit one or more messages including information associated with the generated tracked medical event record to a requester.

In another example embodiment a medical event tracking computer system comprises at least one memory configured to store a plurality of tracked medical event records, each tracked medical event record including a unique medical event tracking number and corresponding to a tracked medical event in relation to a patient, at least one network communication interface, and a processing system comprising at least one processor. The processing system being configured to: obtain information associated with the patient from at least one electronic health record system and at least one medical laboratory information system via the at least one network communication interface; in response to a first request, display information from one or more tracked medical event records stored in the at least one memory for the patient, the displayed information including information obtained from the at least one electronic health record system and the at least one medical laboratory information system; in response to a second request received in relation to the displayed information of a first tracked medical event record, identify, in the at least one memory and based on respective unique medical event tracking numbers included in corresponding records, a second one or more tracked medical events and a third one or more tracked medical events occurring before and after the event corresponding to the first tracked medical event record, respectively; and dynamically display information from one or more of the one or more second tracked medical events and/or the third tracked medical events. Corresponding method and computer-readable media embodiments are also described.

BRIEF DESCRIPTION OF THE DRAWINGS

These and other aspects and advantages will be described in detail with reference to the accompanying drawings, in which:

FIG. 3 illustrates a Quality Assurance Module Coding System, according to some embodiments;

FIG. 4 illustrates a default setting for International Classification of Diseases Version 10 (ICD-10) codes and example default codes, according to some embodiments;

FIG. 9B and FIG. 9C show example living portable document format documents, according to some embodiments;

DETAILED DESCRIPTION

Figure 1:
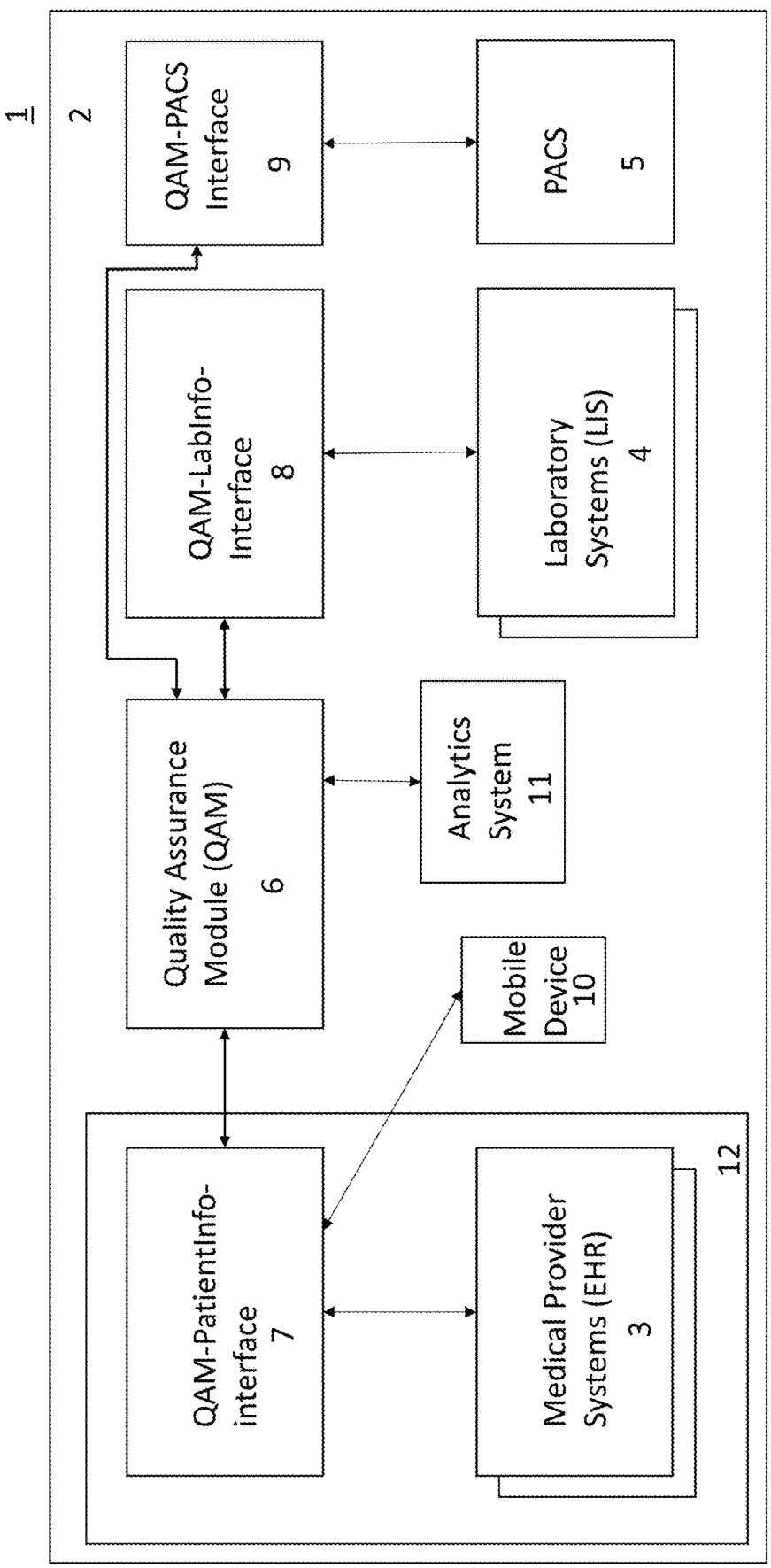
FIG. 1 is an illustration of an environment in which medical service provide computer system, laboratory information systems, and imaging center systems are interconnected by the quality assurance system.

To maximize medicine's full potential, in terms of patient safety, quality, and efficiency, medical data must be tracked differently from how it is done at present. Rather than tracking a patient's PMI linked to a medical event, such as, for example, a biopsy or imaging report, embodiments described in this disclosure adopt an EHR communication system that tracks a medical event with a shared tracking number and links the event to the patient, a process referred to herein as medical event tracking (MET).

A chain-of-custody approach, such as that used in the package delivery industry, is adapted and employed in the tracking of trackable medical events such as, for example, biopsy specimens, clinical pathology reports, and radiology reports. However, rather than simply tracking a physical object, the medical event tracking number in embodiments can link all associated communication and documentation between care providers, laboratory personnel, and the patient. Alerts, notes, patient communication, and future events are incorporated into this solution, in some embodiments, to effectively close the treatment loop.

MET assigns a unique medical event tracking number to each trackable medical event (also referred to as "tracked medical event"), which creates a digital space for the care continuum to interact, sharing information, quality metrics, outcomes, and common medical data storage. MET can also enable direct patient engagement. Linking tracking numbers for each patient's care team interaction creates a linked care continuum communication platform involving the patient and all the care providers relevant to the tracked event.

Unique to MET is the concept of medical data life cycles (MDLC). Each medical event has a definable life span. For example, a benign skin biopsy has a relatively short MDLC and associated event documentation. The associated event data includes tracking the physical location of the specimen to the lab, communication of the report to the physician, and notification of the patient of the benign diagnosis.

In contrast, a skin biopsy demonstrating a melanoma has a MDLC that lasts the lifetime of the patient. This event data would include the same initial linked data as the benign biopsy but would also include tracking numbers for special stains, genetic studies, pharmacological treatments, and future skin examinations. The initial tracking number serves as the reference key to which all subsequent linked events are digitally attached.

With each MET diagnosis there is an associated MDLC which defines the expected time for a patient to be treated completely for each diagnosis. When a treatment is completed this is called "closing the treatment loop". Patients will have many MET diagnoses during their life-time most of which will have short MDLC time spans such as the benign nevus. Some MET diagnoses will last the entire life of a patient such as the diagnosis of melanoma or diabetes for example. These MET diagnoses with a longer MDLC duration create the basis for a new EHR active problem list for which patients are being treated. The current EHR problem list is a simple word document with an ever-expanding group of patient diagnosis. Through creation of MET diagnosis and MDLC problem lists, all MET linked data is integrated for every provider caring for the patient. All current data and future medical results from any provider across the care continuum are automatically sent into the MET EHR problem list. Also, uniquely, the infrastructure integrates medical data from a patient's mobile platform into the MET diagnosis problem list. Linking the MET diagnosis to a patient's mobile platform enables personal wellness/medical devices such as, but not limited to, a glucose meter, FitBit™, or any existing or yet to be created platform to send data to the appropriate location defined by the MET problem list. Previously, before the MET in example embodiments, patient-reported outcomes measures (PROM) using mobile platforms could not be integrated into the EHR to obtain its maximum utility.

In some embodiments, the patient may initiate, via input to an interface provided on the mobile platform, the taking of a monitoring measurement or administering of a treatment by the patient's mobile platform (e.g. mobile platform 10) and/or a personal wellness/medical device communicatively connected to the mobile platform. In some other embodiments, the taking of the monitoring measurement or the administering of the treatment by the patient's mobile platform and/or the connected personal wellness/medical device may be initiated by the QAM 6 in accordance with a follow-up activity associated with a stored medical event tracking record for the patient. In both cases, whether the operation is patient-initiated or is QAM-initiated, a result and/or report of the monitoring, measurement or treatment operation is received at the QAM 6 from the mobile platform 10. The received result and/or report is stored in association with the tracked medical event which caused the result and/or report, and may or may not be stored in its own medical event record. This enables such results and/or reports to be automatically associated with the appropriate specific Medical Data Life Cycles and Medial Event Tracking Numbers. Optionally, the result and/or report, or part thereof, may be displayed on the mobile platform for input from the patient in the form of confirmation or comment that may also be stored in association with the result and/or report.

An additional key step in the MET process according to some embodiments enables a physician to recommend future events, communicate instructions to the care team, and create time metrics to make sure care is delivered in a timely manner For example, when a diagnosis of melanoma is made, the pathologist links a recommendation of excision by attaching a code to the tracking number.

This recommendation code may link a series of time metrics for calling the patient, scheduling the excision, and finally excising the melanoma. The entire care team, including the pathologist, physician, and patient, is notified when appropriate steps are not taken in a specific timeframe. The ability of an individual physician to link future events with quality controls in this way has not existed in medicine before MET. Using MET with pathology reports means that the system may operate with no specimen being lost, every pathology report being received by the physician, every patient being notified of key events in the diagnosis and treatment, every cancer being treated, and future care being accurately coordinated.

Significantly important is the ability to link one medical event to a subsequent medical event. For example, a MET tracking number for a biopsy demonstrating a metastatic cancer is linked to recommended body CT scans which have unique MET tracking numbers, which are in time linked to chemotherapy MET numbers. The MET tracking links related medical events over time. All linked MET data is sent to the "living PDF file" which is another key advance with MET. The "living PDF file" eliminates "chart flipping" or the need to move from a pathology report to another section of the chart to determine if a patient received treatment. Through embedded tracking numbers in PDF pathology reports, future linked medical events are retrospectively added to linked PDF files. By simply hovering over the pathology report, care providers can see the full sequence of events linked to the report. In this manner, tracked event information updates are sent "back-in-time" to prior reports so that any pathology report describes all subsequent related future events. Living PDF files with enable organizing events according to MET tracking numbers in a window hidden behind the PDF interface where linked data is stored for view when the cursor is placed over the designated area. Uniquely, linked MET tracking numbers empower physicians to associate related past and future medical events for purposes, such as, for example, determining the reasons as to why certain sequential events occur and who is coordinating care. The MET thus creates a new learning environment that has not existed in medical care. Every physician gains knowledge through data feedback of outcomes.

The MET platform may provide a software between the EHR and the lab information software (LIS) or Radiology Picture Archiving and Communications System (PACS), in the application program interfaces (API) to interface with the EHR and the LIS or PACS. Using this software bridge between the EHR, LIS, or PACS, the MET software creates a unique medical event tracking number shared by the practice, pathologist, radiologist, patient, courier, medical malpractice company, and insurance company. Utilizing the EHR computerized physician order entry (CPOE) system for ordering a biopsy, image study or lab, the tracking platform creates the unique tracking number and a radiofrequency identification device label (RFID), which is affixed to the specimen bottle. The patient (using an application), the physician, the pathologist and the radiologist are simultaneously linked to the entire data life cycle of the event. Every stakeholder tracks the physical location of the specimen from the office to the lab with all parties receiving real-time notifications about all specimen location transitions.

The MET, according to some embodiments, may be used to coordinate the entire care team interaction, integrate genetic testing, integrate pharmaceutical therapy, track patient outcomes, integrate patient mobile devices, and enable expanded research.

Adoption of integrated MET across the care continuum addresses care interoperability issues, creates shared quality metrics, addresses communication deficiencies, and creates a dynamic patient-centric medical record. Because MET allows any EHR platform to integrate and enables shared, harmonizing data configurations, it provides passive data integration that creates the continuity of the care records, all of which passes through the patient's hands creating the dynamic patient-centric record. In some embodiments, QAM 6 may be configured to support queries and/or data retrieval initiated by authorized EHR systems, LIS systems and/or PACS systems.

Creating a shared taxonomy for assessing data quality addresses the five dimensions of EHR data quality: completeness, correctness, concordance, currently, and plausibility. These features allow high quality data to be stored and presented in a manner that is usable, providing reliable, accurate, and actionable information. This approach may eliminate the highly variable correctness and completeness results observed with current HL7 EHR software.

The MET, according to some embodiments, standardizes quality metrics, eliminates inconsistency across data elements, provides real-time information and communication, allows data segmentation, tracks completed tasks, stores information prospectively, integrates data retrospectively through embedded PDF tracking numbers, and unifies the data storage between the care partners. The system generates clinical quality measures though defined data life-cycle communication and performance metrics of the care team, thus documenting care transitions and outcomes. Example quality metrics/measures metrics may include, for example, treatment recommendation completion percentages per diagnosis and/or per care provider, patient compliance with recommended follow-up percentages, statistics relating recommended procedures to diagnosis, etc. that can be automatically calculated by the QAM 6 from the stored tracked medical event records. With the unique MET integration across the one or more care team EHRs, example embodiments enable advancing beyond the American Society for Testing and Material (ASTM) Standards used by all traditional EHRs to the dynamic MET based data organization.

Additionally, MET allows medical practices and communities to accurately measure performance, identify care delivery and workflow issues, and make needed corrections to deliver the highest quality, evidence-based care. It also allows for efficient transition to value-based payments.

With MET technology, according to some embodiments, users and developers can create customized templates that integrate into their clinical workflows and maximize data completeness, creating an efficient structured data entry system (SDES). They can also adjust templates to physician preference based on encounter-specific variables, such as diagnosis, complaint, or other findings, to create structured data narratives.

Because MET provides unique API software insertions between systems, costly EHR upgrades are unnecessary or minimized; there is little or no additional cost for extraction software or services, system reconfiguration, or developing or purchasing reporting and analytics software. MET adoption has little impact on physician and staff workflow, thus minimizing the time and expense of staff training. In addition, little staff time is required to perform the data quality review and resolution process.

With the creation of high-quality real-time data, MET data enables the primary and secondary uses of data and supports the development of a learning health care system. Real-time data can be used to drive quality improvement, performance reporting and benchmarking, and clinical decision support; create the patient engagement digital space; foster payment reform and pay-for-performance; support health services research; and develop the next generation of patient-centric medical records that move beyond HIEs.

Through MET tracking number linking of the entire care continuum, a Quality Care Medical Market place is created where providers demonstrate their care in comparison to their peers, health networks, and government agencies. This empowerment provides physicians and health networks to negotiate for higher reimbursements and better position themselves with insurance company negotiations. This provides the basis for value base payments plans proposed by the Center for Medicare and Medicaid Services.

FIG. 1 illustrates a medical quality assurance system 2 configured for MET deployed in a network 1 interconnecting one or more electronic health record systems (e.g. EHR systems) 3 and one or more medical laboratory information systems (LIS) 4 and Picture Archiving Communication Systems (PACS) 5, according to some example embodiments. The medical quality assurance system 2 includes a quality assurance module (QAM) 6, a QAM—patient information system application programming interface (API) 7, a QAM API for the LIS 4 and a QAM API for PACS 9. In some embodiments, the medical quality assurance system 2 may also include a patient interface that can be accessed by a patient using, for example, a mobile device 10. In some embodiments, the medical quality assurance system 2 may also include, an analytics system 11.

The EHR systems 3 may be computer systems and/or networks deployed in physician's offices, hospitals, health insurers and/or other entity that has or require access to patient information. The systems 3 typically interfaces with the patient, initiates patient diagnoses and treatments, and stores patient information including PMI (e.g. patient name, date of birth, address, social security number, etc.) and patient's diagnoses and treatments. Typically, patient diagnoses, testing and treatments are initiated as a result of a patient's visit to a doctor's office or other facility that includes an EHR system 3.

The LIS 4/PACS 5 may be deployed at respective laboratories and/or testing facilities. A LIS system 4 typically receives a sample or order from a physician including an instruction and/or proposed diagnosis from an EHR system 3, and returns the results of the requested test. As described in relation to FIG. 2, the testing is performed on a specimen that is transmitted from the physician's office/hospital to the testing facility from the electronic communication between the corresponding EHR system 3 and LIS 4.

Figure 12:
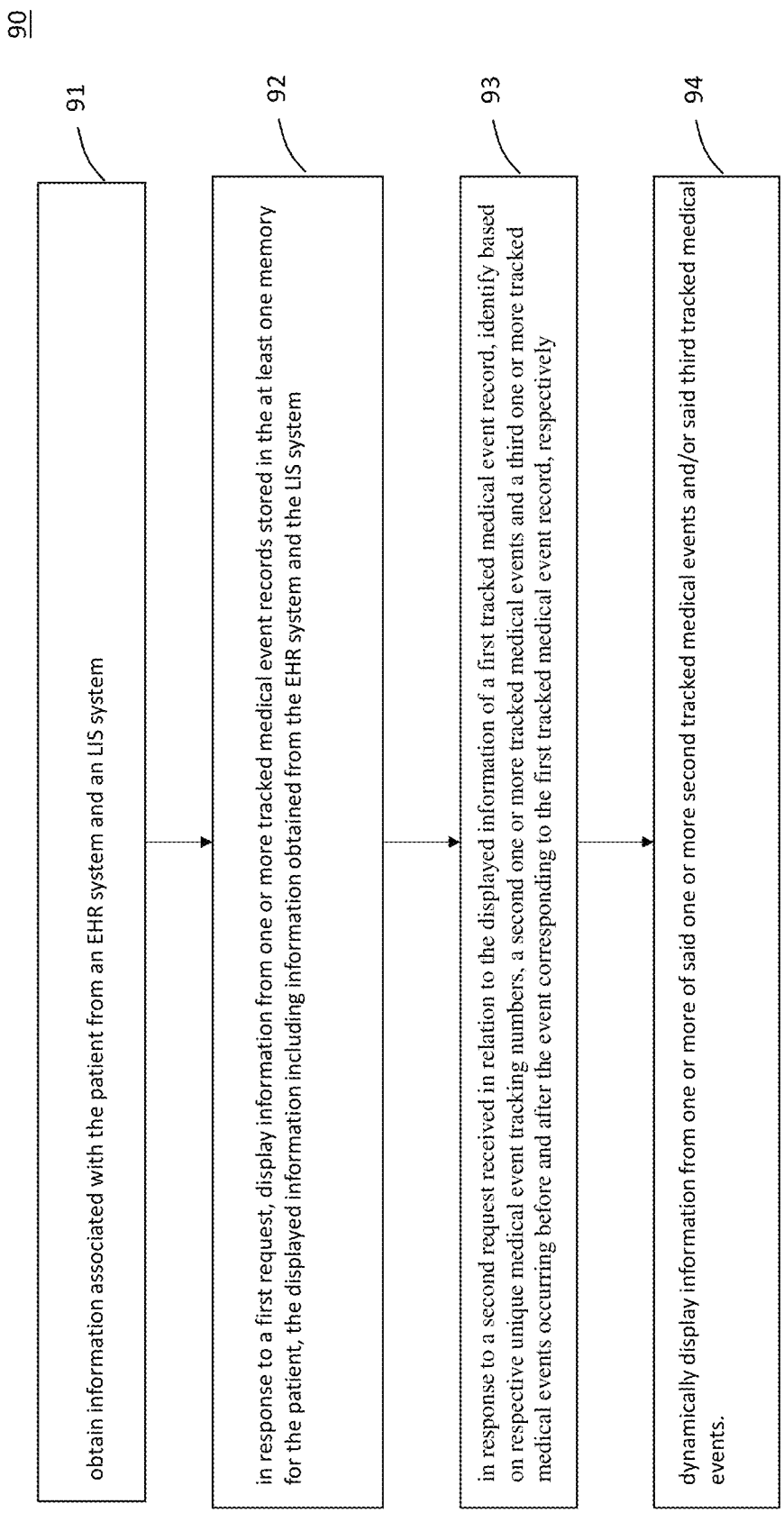
FIG. 12 illustrates a flowchart for a process for a living PDF in accordance with some example embodiments.

Each of systems 2, 3 and 4 may include one or more processing systems, such as, for example, that is described in relation to FIG. 12, and connect to one or more networks via respective network communication interfaces such that the systems 3, 4, and 5 can communicate through network 1.

At least in some embodiments, the systems 3, 4, and 5 may be using a standardized medical environment such as, but not limited to, HL7. In some embodiments, the systems 2, 3, 4, and 5 may each be in a respective network administrative domain. In some embodiments, two or more of systems 2, 3, 4 and 5 may be in the same network administrative domain.

The medical quality assurance system 2, according to embodiments described herein, enables communication and tracking of medical events between respective EHR systems 3, respective LIS systems 4 and PACS systems 5. The communication and tracking of medical events enabled by the medical quality assurance system 2 improves efficiency of communication and coordination between the different participants in a patient's diagnosis and/or treatment, provides for "closing the loop" between the different participants in the patient's diagnosis and/or treatment, and likely reduces errors in diagnosis and treatment.

The API 7 provides for interaction between the EHR system 3 and the medical quality assurance system 2. The API 7 may also provide for the patient to interact with the medical quality assurance system 2 using a mobile device 10 or the like, for example, to display one or more screens of patient information and/or medical events associated with the patient. In some embodiments, the API 7 may maintain a mapping between the patient identifying information (e.g. one or more of patient name, date of birth, social security number) that is used to identify records in the EHR systems 3 and unique medical event tracking numbers that are used to identify records in the system 2.

The LIS API 8 and PACS API 9 provide for interaction between the LIS 4 and PACS 5 and the medical quality assurance system 2. The API 8 or API 9 may maintain a mapping between unique medical event tracking numbers that are used to identify records in the system 2 and any tracking numbers used internally to the LIS 4 and PACS 5. In some embodiments, however, the LIS 4 and PACS 5 may identify its stored records using the respective unique medical event tracking numbers.

In some embodiments, analytics system 11 may provide access to the medical event records stored in the medical quality assurance system 2. With access to the records in system 2, subject to any related restrictions and regulations, the analytics system can be configured to perform analysis using the medical event records of medical events of patients from one or more EHR systems 3. In some embodiments, such analytics is facilitated, by not having any personally identifiable information of patients in the medical event records stored by the QAM 6.

In some embodiments the analytics, based on the patients of all EHRs 3 connected to the system 2 provide information about diagnosis and treatments, such as additional tests being recommended for particular health conditions. Such information can be used for predictive analytics and/or can be used in adding new or changed recommendations to treatment plans.

In some embodiments, a security domain 12 may be configured to apply to accessing any patient data stored in association with one or more of the EHR systems 3 and the APIs 8 and 9. The security domain 12 may ensure a higher level of security and/or authentication within the domain, that in the rest of the medical quality assurance system 2.

Figure 2:
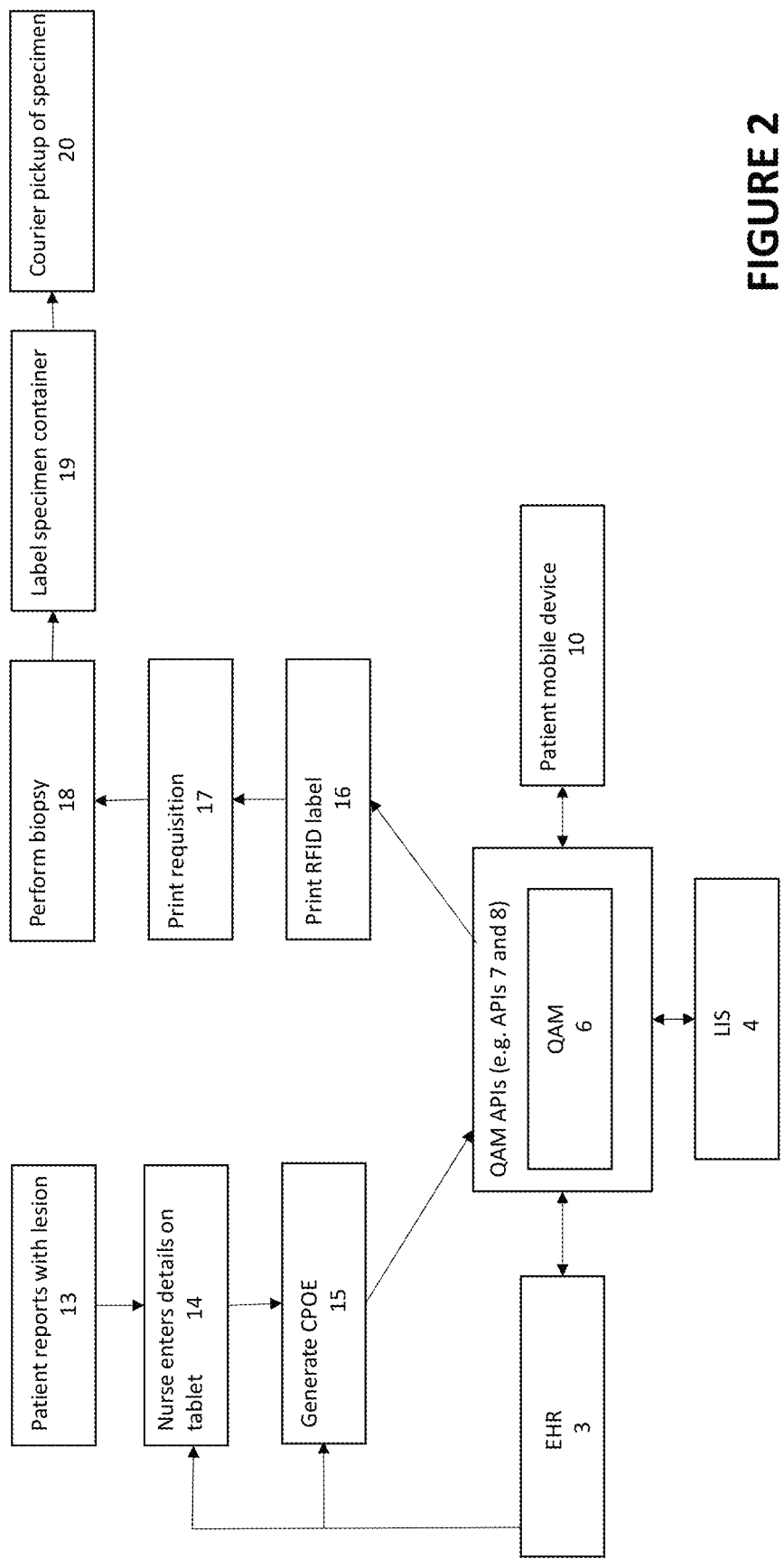
FIG. 2 is a flow diagram showing the patient visit, according to some embodiments.

With reference to FIG. 2, in the scenario of a patient presenting with a possible melanoma 13, the following protocol is followed. A nurse with a procedure tablet or the like 14 having diagrams representing the area to be removed such as a human figure, an ear, or a colon, etc. will electronically, upon touching with a pen, label the specimen as to right, left, and specifics as to the location on the body using an electronic interface. Once the nurse touches the lesion diagram on the tablet, a computer physician order entry (CPOE order) is generated 15 and sent from the EHR 3 to the QAM 6. The QAM 6 receives the CPOE, assigns a unique MET tracking number, organizes relevant data, and forwards information to the LIS 4 using the LIS API 8. The QAM sends the unique tracking number (e.g. over the web and/or via the lab API 8) to printer, prints labels in the physician's office 16 and prints the requisition 17. The biopsy is performed 18, and the specimen is labeled 19. Subsequently, the courier takes the specimen to the lab 20. The information generated by the physician's office CPOE (generated at 15 in FIG. 2) includes the patient name, date of birth, patient demographics, and the physician's specimen number, location on the body, insurance information, and the physician's differential diagnosis. The QAM 6 generated unique tracking number is used to identify the specimen on arrival to the lab and be used to track the specimen carried by the courier. A label is printed with a unique linked tracking number (tracking number 32 in FIG. 6). The specimens are placed in a sealed bag accompanied by a printed document (e.g. the requisition printed at step 16) that contains the information generated by the sending physician and receiving lab all of which is linked to the unique tracking number. Once the specimens are labeled (e.g. at step 16 in FIG. 2) with the scan codes and RFID, and printed summary document (e.g. the requisition document at step 17) is placed in the specimen bag, the information is sent electronically to the lab by the QAM 6. The specimen information delivered to the lab is integrated with the lab's LIS 4 for processing the specimens with the unique MET tracking number, information for billing, and for integrating with the QAM 6. The courier is able to use the scan codes/RFID generated to document times of pickup and delivery. The information sent from the QAM 6 to the lab is integrated with the LIS 4 for the accession of the specimen and for the pathologist to render a diagnosis.

With reference to FIG. 3, the pathologist renders a diagnosis and using the Quality Assurance Module Coding System 22, attaches the ICD-10 Diagnosis 23, procedure recommendation code 24, time interval 25 and referral code 26. Information is sent from the Lab LIS 4 to the Lab API 8, and intercepted by QAM 6. The linked data is then sent from the QAM 6 over the LIS API 8 to the EHR 3. The Quality Assurance Module Coding System 22 enables closed loop communication through linking future events (tracked medical events that occur in the future) to a time interval. If the future events do not occur, the patient, pathologist and physician are notified.

Traditionally, a pathologist renders a diagnosis and occasionally an additional recommendation would be written in the "fine print" of the pathology report. Unfortunately, the "fine print" recommendations are overlooked and as not part of the formal diagnosis and are not recorded in an Electronic Health Record software system. This is a serious defect in the current EHR systems.

There are many examples of how the "fine print" recommendations in pathology and radiology for example can have tragic outcomes for patients. If a patient has a pigmented mole removed to check if the lesion is a melanoma, the pathologist may only see a portion of the entire lesion, which under the microscope is benign or non-cancerous. The pathologist may note in the report that the mole extends beyond what he can see and is worried that the diagnosis melanoma is still possible. Surprisingly, the only diagnosis codes (ICD-10) Medicare has approved for the pathologist to use is Cancer or Benign. There are no codes that allow a pathologist to recommend additional testing. Additionally, there is no communication tool to effectively deliver "fine print" or additional recommendations from pathologist to the referring physician or patients. In the melanoma scenario employing the QAM, the pathologist has unique codes created through the Quality Assurance Module Coding System 22 that allows him or her to communicate that the mole examined is "Benign or non-cancerous" but he recommends additional excision, biopsy, or additional examination of the patient. He is also provided with the capability to communicate a time parameter for completing his recommendation.

Radiologists face this issue every day with every test they perform. The mammogram is a tragic example of how this can have a fatal outcome for a patient. The radiologist may examine a mammogram which is normal but a small area may be of concern but not enough to diagnose as a "cancer." The radiologist must convey a recommendation, but no codes are available to communicate with the ordering physician or patient that additional testing is necessary and how soon additional testing is needed. In FIG. 3, the Quality Assurance Module Coding System 22 creates a unique set of codes selected by the radiologist, that are linked with the diagnosis codes 23 to define additional recommendations 24, time intervals 25, and referral codes 26 for procedures needed to close the recommended treatment loop.

The basic format of the "fine print codes, or additional recommendations" is demonstrated in the Quality Assurance Module Coding System 22 shown in FIG. 3. The codes include a procedure recommendation 24 followed by a time interval 25 for completion and a referral recommendation 26. The procedures recommended vary by specialty such as pathology, radiology, etc. As an exemplary system, the pathologist may recommend several procedures after a biopsy such as recommending the patients have a follow up exam, biopsy, excision, excision with wide margins, or recommend sending additional specimens to a specialist (e.g. referral codes 26). These codes are then combined with a numerical code attached to a time interval line by day, week, month, or year (e.g. time interval 25). The pathologist for example could recommend a repeat biopsy one week from now, which as shown in FIG. 3, would be coded as 02.12/00.

The radiologist has a similar arrangement of codes with procedures, time intervals, and referral recommendations. The radiologist may recommend a repeat procedure, plain films, CAT scan, magnetic resonance imaging, mammogram, ultrasound, biopsy (e.g. procedure codes 24 for radiology shown in FIG. 3) or another test. Additionally, a recommendation may be made for referral to another specialist such as a surgeon, oncologist, radiologist, neurologist, or other specialist (e.g. referral codes 26). A radiologist may see a suspicious area on a mammogram and recommend a repeat mammogram in six months. The diagnosis would be a benign mammogram but the additional code would signify a follow-up exam, for example, 01.63/00. If the radiologist recommended a biopsy by a surgeon within the week, another code would use, for example, 07.12/01.12.

In addition to the customizable codes 22, a group of default QAM codes are defined for each test, as for example, shown in FIG. 4. In addition to the QAM Coding System 22, there are default codes with time metrics for ICD-10 diagnoses. FIG. 4 shows the schema for example default settings ICD-10 codes 27. The default recommendations can be specialty standards for future examinations or procedures. For example, a diagnosis of melanoma would have a default recommendation of an annual skin exam or a breast lesion for 6 months follow-up mammograms.

Figure 5:
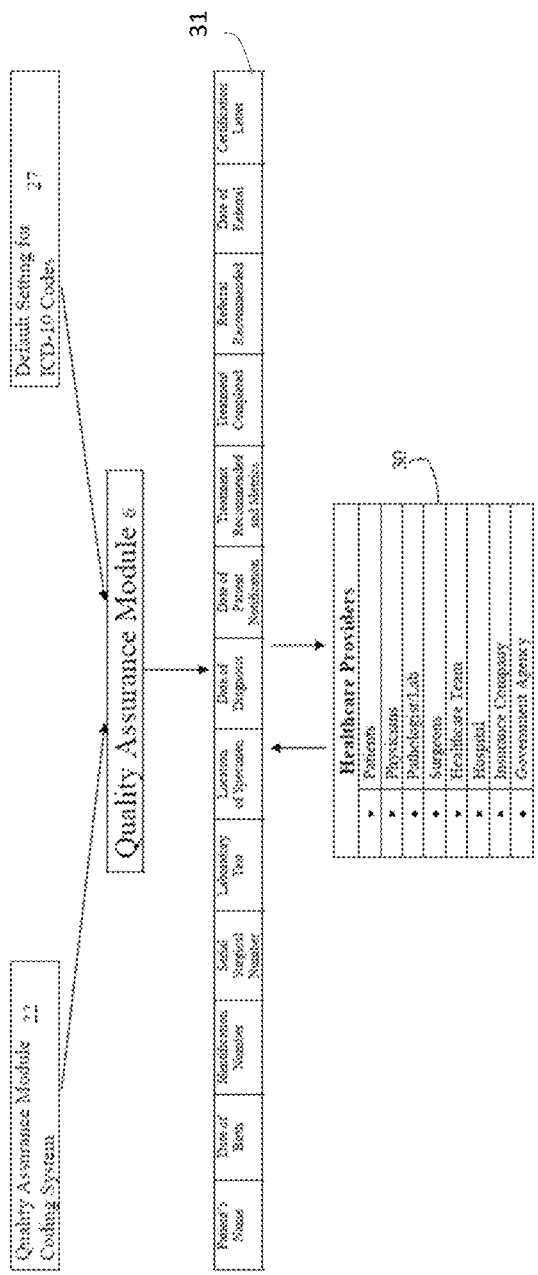
FIG. 5 is a flow diagram showing the Quality Assurance Module, according to some embodiments.

In both examples, the diagnosis ICD-10 code 23 is combined with a default setting 27 as shown in FIG. 4, and this information is sent to the QAM 6. FIG. 5 illustrates some aspects of the interface of the Quality Assurance Module 6 where healthcare providers, patients, and/or others 28 communicate with the QAM 6. Codes from the Quality Assurance Module Coding System 22 and the default settings 27 are integrated. All health providers use the same interface, and all recommendations, referrals, and time intervals can be followed.

Additionally, programmed with the QAM 6 are a biopsy default time metrics specific for various diagnoses/procedures. For example, if one has melanoma, a time clock or metric is initiated allowing 10 days for the physician to contact the patient. If contact with the patient is not made, emails, text messages or other alerts are sent to the physician, and after a certain amount of time, there is a direct email sent, test message and/or other alert to the patient about the outstanding diagnosis. With reference to FIG. 5, for each step of the process, diagnosis of the specimen, notifying the physician, notifying the patient and documentation of treatment closure, all parties are notified. When additional procedure or referral may be recommended the information is placed on the QAM with a time metric as to when the additional procedure is scheduled and what time frame the procedure should be completed (e.g. time interval 25). If these steps do not occur in a timely mariner, the system automatically sends emails, text messages and/or another type of alert to the physician, the pathologist, the referral specialist and/or the patient. If the patient does not respond and the recommended procedure is not completed, a certified letter is generated electronically and sent to the patient closing the loop for the entire procedure. The certified letter notifying the patient that the treatment is incomplete is generated by the QAM 6.

Via mobile platforms 10, the system notifies patients of each step their medical event takes along the process. Patients are notified when and where specimens are sent from the physician's office, date of arrival at the lab, date of arrival of the information at the physician's office, date of patient notification of the diagnosis, any additional recommendations or treatments, dates of future procedures, and dates of communication with certified letters.

The QAM 6 can provide the patient or one or more healthcare providers 30 associated with a patient and/or diagnosis a combined record or report, such as, for example, 31 for use by the patient or the one or more healthcare providers. The surgical field also benefits from the QAM 6. A diagnosis such as a colon polyp or bronchoscopy may require scheduled follow up visits or testing coordinated via the default settings ICD codes 27. Placing these recommendations on the QAM 6 will assure compliance with the recommendations. The emergency room would benefit from a system following patient compliance for recommendations of following up with additional physicians or testing.

The pathology lab benefits by saving employee time and money not having to re-input data already recorded at the referring physician's office, having better documentation of result delivery to physicians and patients and follow up on recommendations. The referring physicians save time and costs with the QAM 6 standardized follow up, and patients benefit through continual contact which allows the process to improve communication and safety.

In the radiology field, the process is similar to the pathology scenario. Patient demographics are transmitted from the EHR 3 using the CPOE (e.g. generated at 15) over the PACS API 9 with the x-ray order to the radiologist who performs the x-ray. The diagnosis rendered may require additional tests and recommendations. The additional tests or recommendations are placed on the QAM 6 with time metrics to assure they are completed. The system assures that patients receive recommended care.

The QAM may be located on the system servers in the "Cloud," accessible by the lab, physician, patient, hospital, insurance company, government agencies and other healthcare team members.

The quality assurance process described with reference to FIGS. 1-5 is preferably a browser-based system in which a program running on a user's computer (the user's web browser) requests information from a server program running on a system server. The system server sends the requested data back to the browser program, and the browser program then interprets and displays the data on the user's computer screen. The process is as follows:

1. The user runs a web browser program on his/her computer.

2. The user connects to the server computer (e.g., via the Internet). Connection to the server computer may be conditioned upon the correct entry of a password as is well known.

3. The user requests a page from the server computer. The user's browser sends a message to the server computer that includes the following:

the transfer protocol (e.g., http://); and

1the address, or Uniform Resource Locator (URL).

4. The server computer receives the user's request and retrieves the requested page, which is composed, for example, in HTML (Hypertext Markup Language).

5. The server then transmits the requested page to the user's computer.

6. The user's browser program receives the HTML text and displays its interpretation of the requested page.

Thus, the browser program on the user's computer sends requests and receives the data needed to display the HTML page on the user's computer screen. This includes the HTML file itself plus any graphic, sound and/or video files mentioned in it. Once the data is retrieved, the browser formats the data and displays the data on the user's computer screen. Helper applications, plug-ins, and enhancements such as Java™ enable the browser, among other things, to play sound and/or display video inserted in the HTML file. The fonts installed on the user's computer and the display preferences in the browser used by the user determine how the text is formatted.

If the user has requested an action that requires running a program (e.g., a search), the server loads and runs the program. This process usually creates a custom HTML page "on the fly" that contains the results of the program's action (e.g., the search results), and then sends those results back to the browser.

Browser programs suitable for use in connection with the account management system of the described embodiments include Mozilla Firefox® and Internet Explorer available from Microsoft® Corp.

While the above description contemplates that each user has a computer running a web browser, it will be appreciated that more than one user could use a particular computer terminal or that a "kiosk" at a central location (e.g., a cafeteria, a break area, etc.) with access to the system server could be provided.

It will be recognized by those in the art that various tools are readily available to create web pages for accessing data stored on a server and that such tools may be used to develop and implement the system described below and illustrated in the accompanying drawings.

Figure 6:
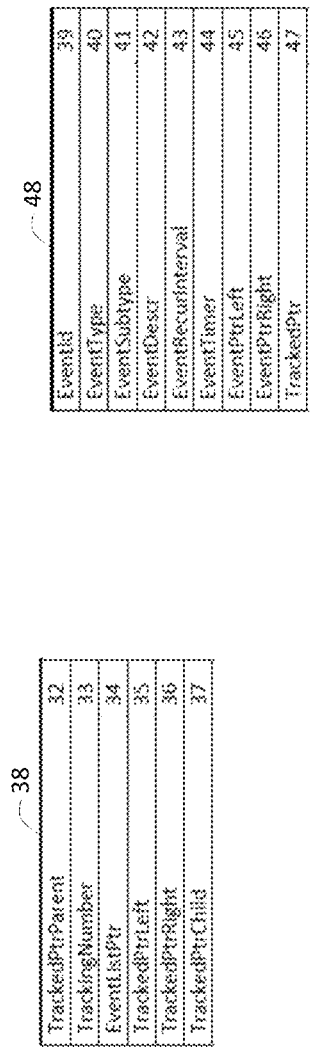
FIG. 6 illustrate an example arrangement of medical event records, according to some embodiments.

FIG. 6 illustrates example data structures for medical event records stored in the QAM 6, and the arrangement of related medical event records in the memory of the QAM 6, according to some embodiments. In the illustrated embodiments, a two-level record structure is employed for the medical event records stored and maintained in the memory of the QAM 6. A first type 38 of record is used to identify tracked medical events, and a second type 48 of record is used to store all other medical events stored in the QAM 6.

A tracked medical event is a medical event that is to be tracked by the system, and the tracking of which is used in order to improve the completion of diagnosis and treatment plans. Example tracked events include, but are not limited to, pathology specimens, image studies, referrals, any event which requires additional intervention and other lab processed information about the patient.

Each tracked event 38 causes one or more event records 48 to be created in the memory of the QAM 6. In one example, in the example of the melanoma diagnosis described above, a tracked event 38 is generated in the QAM 6 for the physician taking the specimen, and a corresponding event 48 is also generated.

In the data structure 38, each tracked event includes a tracking number field ("TrackingNumber") 33 and an event list pointer field ("EventListPtr") 34. The tracking number field takes a unique medical event tracking number as its value. The event pointer field's value is a pointer to an event that is represented in a data structure 48. The tracked event data structure 38 may have additional pointers, such as, for example, a pointer to a parent tracked event ("TrackedPtrParent") 32, a pointer to a child tracked event ("TrackedPtrChild") 37, a left sibling tracked event ("TrackedPtrLeft") 35, and a right sibling tracked event ("TrackedEventPtr Right") 36. This enables each tracked event to be related to other events in the memory of the QAM 6, in a manner that allows for high flexibility in tracking various tracked events in a diagnosis and/or treatment, and also to quickly access the tracked events related to one tracked event.

As noted above, each tracked even points to at least one event data structure 48. The event data structure 48 encodes the information about the event that enables the system to monitor the event. The event data structure 48 includes an event identifier ("EventId") 39, an event type ("EventType") 40, an event subtype ("EventSubtype") 41, an event description ("EventDescr") 42, an event recurrence interval ("EventRecurInterval") 43, an event timer ("EventTimer") 44, a pointer to the corresponding tracked event ("TrackedPtr") 47, a pointer to a left sibling event ("EventPtrLeft") 45, and a pointer to a right sibling event ("EventPtrRight") 46.

When the QAM 6 receives a message for a new medical event from an EHR system 3, the request may include ICD-10 codes as described in relation to FIGS. 3-5 specifying the recommendations (e.g. any of proposed diagnosis, specimen description, referral recommendation, follow-up time intervals, etc.) or such codes may be determined by the QAM 6-patient information system API based on either a predetermined translation from another set of codes specific to an EHR and/or by querying the request initiator. The ICD-10 codes or information determined based on the ICD-10 codes may be stored in the corresponding tracked event records and/or event records.

In the above described example of the melanoma specimen, when the physician submits the initial specimen to the lab, the request from the physician to the QAM 6 causes the QAM 6 to generated a tracked event (e.g. new instance of tracked event record 38 with a new unique medical event tracking number 33 corresponding to the specimen submitted to the lab, and an event chain starting with an event record 48 for the physician visit. Additionally, a second event record 48 is created in accordance with a specified time interval for follow-up and a proposed diagnosis. The new tracked event record points to the first event record in the chain, which in turn points to the second event record. Each of the first and second events may point to the corresponding tracked event record. Both the first and second event records may be configured with timer values either according to system configured event type specific default values or values specifically conveyed in the request.

The QAM 6 implements a timer mechanism to enable each event record to have its own timer value.

In some embodiments, in addition to the above described fields of the data structures 38 and 48, fields may be available in one or more of 38 or 48 to maintain relevant information such as laboratory test, location of specimen, date of diagnosis, date of patient notification, treatment recommendations and metrics, treatment completed date, referral recommended, referral completed date, etc. The QAM-Patient information system 2 operates to, using a maintained mapping of patient identification information in the EHR system 3 to medical event tracking numbers in the QAM 6, dynamically assemble patient information and/or reports combining patient information from EHR system 3, LIS 4 or PACS System 5 and/or referral information from the QAM 6. An example combined record or report 31 is shown in FIG. 5.

Figure 7A:
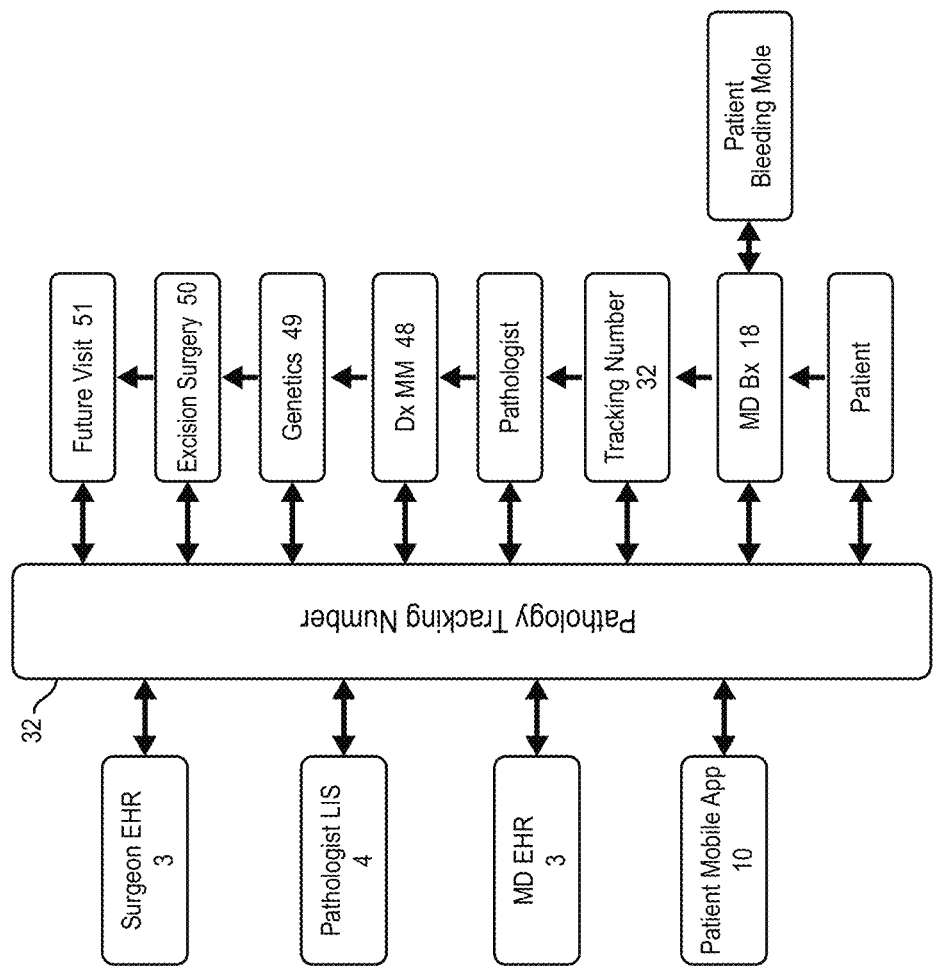
FIG. 7A illustrates an example conceptual view of how the tracking number interrelates physicians and testing, according to some embodiments.

FIG. 7A tracking interrelationship conceptually illustrates how the medical event tracking number is used in certain embodiments, to track an event throughout a diagnosis and treatment cycle for a patient. The illustrated example shows the diagnosis and excision of a patient's bleeding mole that relates the patient, the physician, pathologist and the surgeon. On the left side of FIG. 7A, the patient's mobile app 10, the physician's EHR system 3, the pathologist's LIS system 4, and the surgeon's EHR system 3 are shown. The figure illustrates that they, or more specifically, their respective software systems, are all interconnected by the same medical event tracking number 32 (indicated as "pathology tracking number" in the figure).

By enabling the intercommunication on a common communication platform between the physician, pathologist and the surgeon in relation to the particular pathology specimen via the unique medical event tracking number assigned to corresponding tracked event, embodiments allow recommendations from the pathologist and/or a radiologist be recorded in the patient information such that it is accessible to the surgeon and/or the physician. The unique medical event tracking number thus can link the entire care team for the patient and provide for effective coordination of future testing/procedures. Some embodiments may allow future scheduled events or sequence of events to be changed by any of the providers and/or the patient.

The unique medical event tracking number also enables effective sharing of quality metrics.

The unique medical event tracking number implemented in the QAM 6 using data structures 38 and 48, enables changing the time frame for future events, for example, in radiology one may have less than an hour for a pneumothorax to be corrected, or the severity of a melanoma may mean every 3 months vs every 6 months exams, The unique medical event tracking number also allows documentation of event completion, notification of incomplete event closure, allows data to flow to reports retrospectively in some embodiments so that when a PDF report is read "hovering" over embedded tracking number reveals future linked events.

The unique medical event tracking number enables filing data into patient medical records linked to tracking number. For example, report data from the LIS etc. may be sent to the tracking number which disseminates information to appropriate EHR system 3 and/or appropriate patient mobile platform 10.

FIG. 7A also illustrates the progression of the diagnosis and treatment. To the right of the illustrated "pathology tracking number" 32, starting from the bottom it is shown that the patient visits the physician for the initial biopsy ("MD Bx") 18 of the bleeding mole. The physician takes the sample 18, obtains a tracking number 32, and sends the sample with label attached and tracking number to the pathologist. The physician also communicates electronically with the pathologist regarding the sample and the proposed diagnosis. The pathologist completes his diagnosis ("Dx MM" 48) and requires a genetic test ("Genetics" 49) to be performed. Subsequently, the surgeon performs the excision surgery ("Excision surgery") 50. Finally, a future visit 51 is scheduled. The figure illustrates that all of the events of the initial patient visit to the physician, the sample, the pathologist visit, the pathologist diagnosis, the genetics testing, the excision surgery, and the future visit 51 are all trackable by the same medical event tracking number 32 here referred to as the pathology tracking number.

Figure 7B:
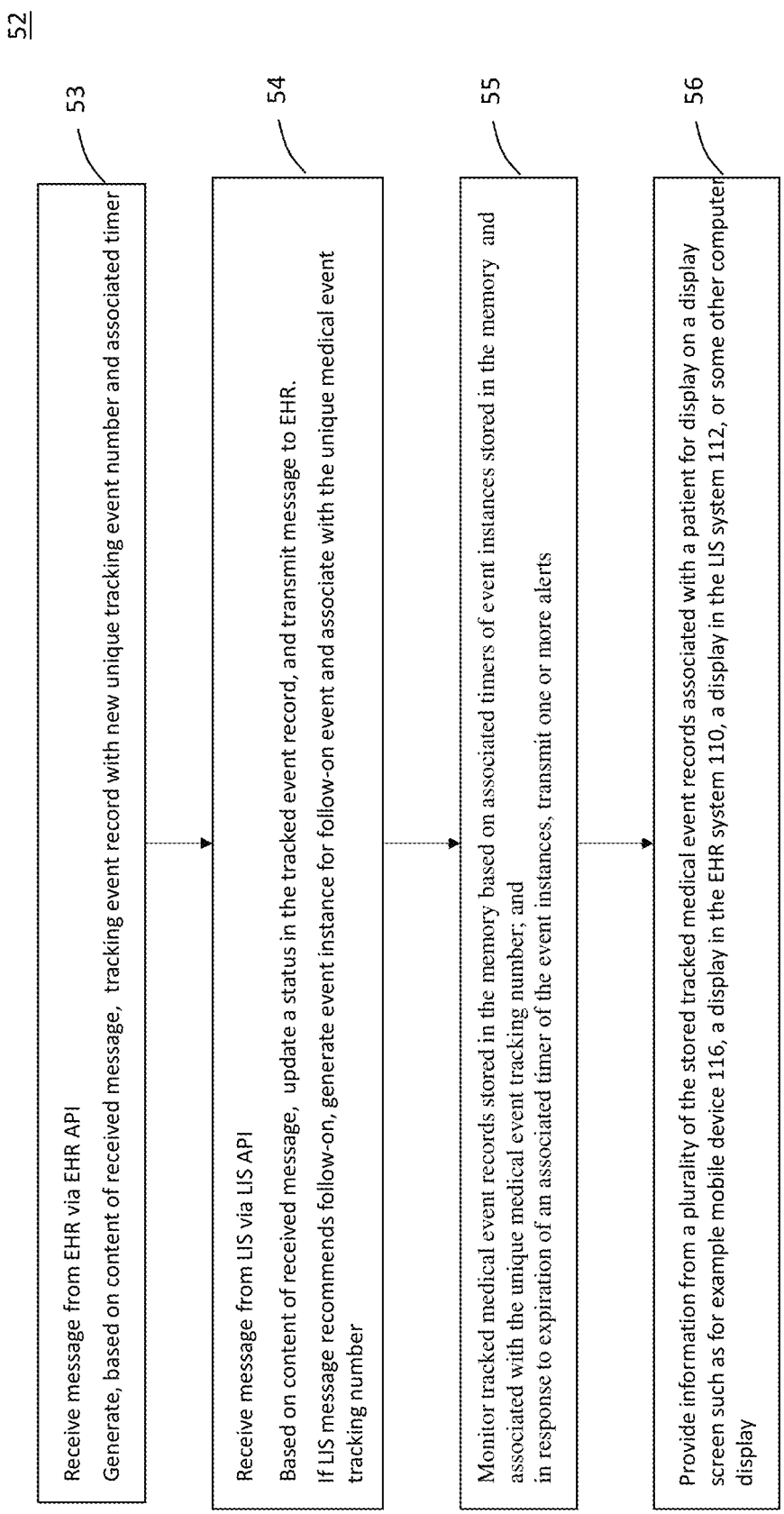
FIG. 7B illustrates a flowchart of a process for tracking and quality assurance of medical events, according to some embodiments.

FIG. 7B illustrates a flowchart for a process 52 for tracking and quality assurance of medical events in accordance with some embodiments. Process 52 may be performed by one or more computers that, via one or more network interfaces, interface to one or more EHR systems 3 and one or more LIS systems 4 or PACS systems 5. For example, process 52 may be performed by the medical event tracking system 2 described in relation to FIG. 1 and other figures, which provides an API 7 interfacing to one or more EHR systems 3 and another API 8 interfacing to one or more LIS system 4 or API interfacing with PACS systems 5. In some embodiments, system 2 may also include mobile device 10 (e.g. used by a patient, medical professional, care provider etc.) and/or analytics system 11.

As an example, process 52 is described in relation to the scenario described in FIG. 2. In the scenario of FIG. 2, when the nurse is ready to generate the label to affix to the specimen one or more messages in a format defined by the interface 7 are exchanged between the EHR system 3 and quality assurance system 2.

In response to the one or more messages received from the EHR system 3, at operation 53, the system 2 generates a unique medical event tracking number 32 to track the specimen excised or to be excised, generates a corresponding tracked medical event record based on a tracked event record structure 38 and at least one event record based on an event data structure 48 in a memory of system 2. System 2 associates at least one timer of the one or more generated event records with the generated tracked medical event record. An event type and/or event subtype and the associated timer of the generated tracked medical event record and/or the corresponding one or more event records are set in accordance with a code included in the received first type of message. A proposed diagnosis communicated from the EHR system 3 may also be recorded in an event record.

Operation 53 may include generating a label for the specimen including, for example, any of patient demographics, the proposed diagnosis, and the generated unique medical event tracking number or another number associated in the memory of system 2 with the unique medical event tracking number. In some embodiments, the label is formed by generating a machine-readable code.

When the pathologist in the scenario of FIG. 2 renders the diagnosis and recommendation, at operation 54, one or more messages as defined by the interface 8 are exchanged between the system 2 and LIS 4. In response to one or more messages received from LIS 4, the system 2 may update a status of the generated tracked medical event record to indicate that the medical event corresponding to the pathologist diagnosis is complete, and may transmit a status message to the EHR system 3.

Based on the diagnosis and/or recommendations encoded in the one or more messages received from LIS 4, system 2 determines whether one or more follow-on medical events is necessary. Then, for each one or more follow-on medical events determined to be necessary, the system 2 generates a new event instance corresponding to the one or more follow on medical events in the memory of system 2, associates the new event instance with the unique medical event tracking number, and associates a timer with the new event instance. An event type and/or event subtype and an associated timer of the new event instance is set in accordance with a code included in the messages received from LIS 4. In some embodiments, a plurality of new event instances is created in the memory of system 2 in response to the messages received from LIS 4, and each of the generated event instances is associated with the unique medical event tracking number 32.

In some embodiments, the one or more messages received from the LIS 4 in operation 54 may include a pathologist diagnosis and a recommendation code from a lab. The system 2, using interface 8, imports (e.g., by performing any necessary conversions) the pathologist diagnosis and the recommendation code 22 to the generated tracked medical event record and the corresponding event records. The recommendation code may identify any additional procedures needed and time parameters for completion. For example, in some embodiments, the recommendation code from the LIS identifies additional procedures including at least one of re-testing the patient, expanding a scope of testing, recommending patient follow-up visits, and/or recommending a referral to another specialist. The recommendation code may further identify time parameters for the recommended additional procedures. In some embodiments, the recommendation code may identify additional procedures including at least one of re-excision of a lesion, excision of the lesion with a specific margin of skin, recommending patient follow-up visits, and/or recommending a referral to another specialist.

Operation 54 may include identifying time metrics for follow-up activity based on the one or more messages from the LIS 4, for example, based on the pathologist diagnosis and the recommendation code. Operation 54 may also include setting a timer associated with an event instance stored in the at least one memory in accordance with identified time metrics, wherein the event instance is associated in the memory of system 2 with the generated tracked medical event record.

When the one or more messages from the LIS 4 includes a recommendation for additional procedures specified in the coding system 22, in response to one of the identified additional procedures, the system 2 may generate a second unique medical event tracking number 32 and a second tracked medical event record, and associate the second tracked medical event record with the first tracked medical event record.

The information relating to the specimen received from the LIS 4 and/or the EHR system 3 may include a date that the specimen was sent to the lab, a location of the lab, arrival date at the lab, arrival date for the pathologist diagnosis at the patient's care provider, date of patient notification of the pathologist diagnosis, additional recommendations or treatments, dates of future procedures, and dates of communications sent to the patient. In some embodiments, the specimen may include an x-ray or other scan.

In some embodiments, the QAM 6 may automatically identify and generate referral recommendations and time metrics, and the corresponding data structures in the memory of the system 2, based on the pathologist recommendation and diagnosis. In some embodiments (see default coding for follow-up mammogram shown in FIG. 4), the system 2 may store a set of programmable rules and/or algorithms that can automatically add additional medical events, such as, for example, referrals and corresponding time and monitoring parameters associated with the same medical event tracking number or a new medical event tracking number that is linked to an existing medical event tracking number, in response to specifically identified recommendations and/or diagnosis being identified in a message from an EHR system 3 or LIS 4. For example, in response to receiving a diagnosis of malignant melanoma from the pathologist, the system may automatically add an event for a follow-up in a predefined time interval (according to a default rule based on the diagnosis) and also a new tracked event, with a new unique medical event tracking number that is linked to the tracking number associated with the received diagnosis, for a re-excision. The system may also automatically update any living documents in which the tracking number associated with the received diagnosis is embedded to include the newly received information.

In some embodiments, with respect to operations 53 and 54, when EHR system 3 and/or LIS system 4 transmits messages to the respective interface 7 and/or 8 using a coding system that is proprietary or different from the coding system used by the system 2, such as ICD-10 coding described above FIG. 3, conversions between those proprietary or different codes and the codes of the system 2 may be performed at the interfaces 7 and/or 8. For example, conversion from a first code in the messages received from an EHR system 3 at the interface 7 to an event type and/or subtype stored in the memory of system 2 in association with a tracked medical event record, and/or conversion from the stored event type and/or event subtype into a second code used in an LIS for messages to/from the LIS 4 may be performed at the interface 8.

The recommendation code used by the system 2 may include default coding sequences that reflect individual physician, practice group, medical society and national preferences.

The system 2, in a continuing operation 55, monitors the tracked medical event records stored in the memory based on respective associated timers of event instances stored in the memory and associated with the respective medical event records. In response to expiration of an associated timer of the event instances, the system 2 may transmit one or more alerts and/or may perform other operations.

Operation 55 may include monitoring the follow-up activity and corresponding time metrics, and automatically sending alerts (e.g. text messages, emails, automated phone call, automated mailings etc.) when the follow-up activity does not take place according to the time metrics. Operation 55 may also include, when the patient, care provider, or lab does not respond to a communication within a preset time period, generating a closed diagnosis letter or message to that entity.

The system 2, in a continuing operation 56, provides information from a plurality of the stored tracked medical event records associated with a patient for display on a display screen such as for example mobile device 10, a display in the EHR system 3, a display in the LIS system 4, or some other computer display. Some example displays are described in relation to FIG. 10. According to some embodiments, in the display, medical events corresponding to the plurality of tracked medical event records are arranged in a first area of the display screen, a first tracked medical event record from the plurality of stored tracked medical event records is associated with a plurality of event instances stored in the memory of system 2, and the plurality of event instances are represented in a second area of the display screen.

In some embodiments, medical events corresponding to the plurality of tracked medical event records are arranged on the display screen, a first area of the display screen displaying past and future medical events associated with a current medical event for the patient and a second area of the display screen displaying one or more other related medical events. In some embodiments, medical events corresponding to the plurality of tracked medical event records are arranged in a first area of the display screen as a tree.

Operation 56 may include the system 2 communicating information relating to any specimen and a status of the diagnosis from any medical professional to the patient. For example, the patient may access the system 2 using a mobile device 10 and a web application. In some embodiments, system 2 may allow a patient and/or other authorized person to make changes to the records stored in the memory of system 2, for example, to make change to the time settings, referral events and the like.

Figure 8:
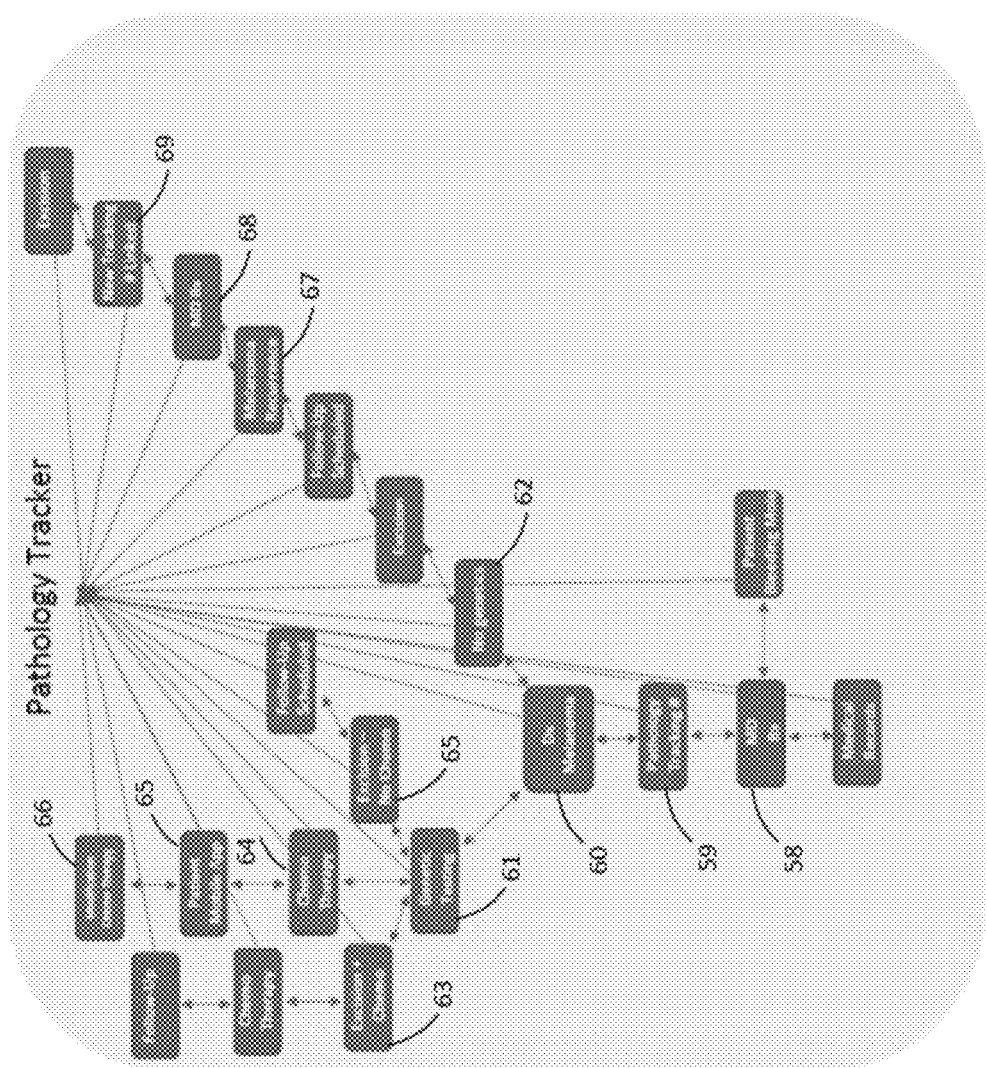
FIG. 8 illustrates an example conceptual view of how the tracking number interrelates physicians and testing, according to some embodiments.

FIG. 8 illustrates another conceptual view of the tracking number associating multiple treatment plans for a particular patient's bleeding mole. Based on the physician's initial diagnosis and sampling at 58 of the patient's bleeding mole, a tracking number is generated at 59 for the pathology sample, and the pathologist determines at 60 a diagnosis of melanoma.

Based on the diagnosis at 60, a treatment path including genetic testing 61 or a path including no genetic testing 62 may be taken. When the genetic testing path 61 is taken, based on the genetic test, one of three paths—a path with excision and chemotherapy 63, a path with chemotherapy and no excision 64 and a path with excision and no chemotherapy 65—may be taken.

The path of 64 illustrates the patient's mobile app introducing a medical event 65 to modify chemotherapy 66.

The path of no genetic testing 62 illustrates a recurrence of the melanoma being detected at 67 in relation to a follow-up visit, and causing a new pathology sample to be taken at 68 (with a new corresponding tracking number being generated 69) for the recurrent melanoma.

Figure 9A:
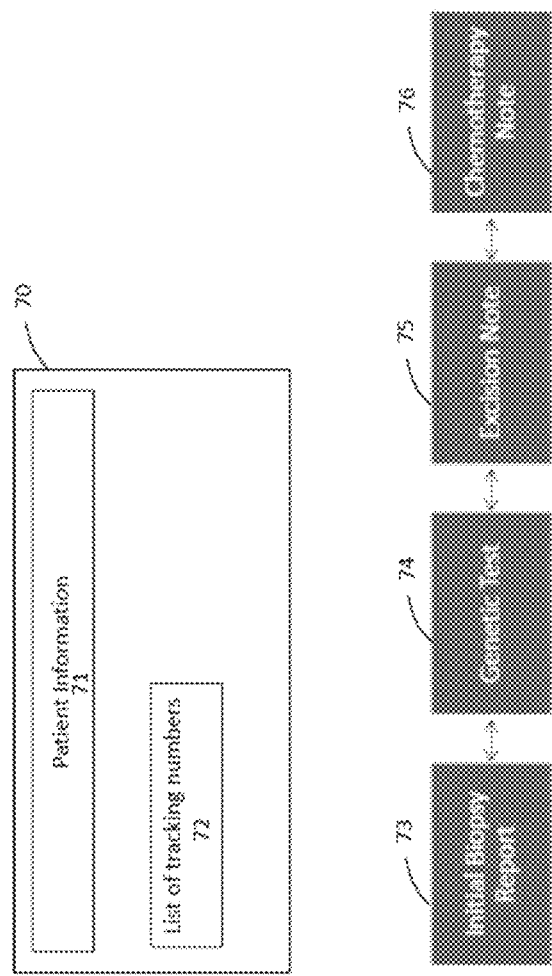
FIG. 9A schematically illustrates an example living portable document format document, according to some example embodiments.

FIG. 9A conceptually illustrates a living portable document file (PDF) document 70, according to certain example embodiments. For example, the living document may be a pathology report PDF.

The living PDF document 70 includes patient information 71 which identifies the patient. Additionally, according to some embodiments, one or more medical event tracking numbers are embedded in the living document. The figure shows a list 72 of embedded medical event tracking numbers. In some embodiments, each of the tracking numbers pertain to a diagnosis and/or treatment plan. In some embodiments, for example, each embedded tracking number may pertain to a respective pathology specimen of the patient.

The living PDF document 70 may be dynamically updated to include the data of each event as each event pertaining to a particular tracking number is completed. All future linked data is sent and/or integrated "retro-actively" to each report along the chain of events associated with the tracking number. As described in relation to the data structures 38 and 48 above, information of the respective related events can be accessed from a particular event by following the pointers from that event's data structure 38 and/or 48.

According to an embodiment, the living PDF document 70 is dynamically updated to include details of all the completed events pertaining to each of the tracking numbers in the list 72. The dynamically included details may be arranged in separate areas for the respective tracking numbers.

Figure 9B:
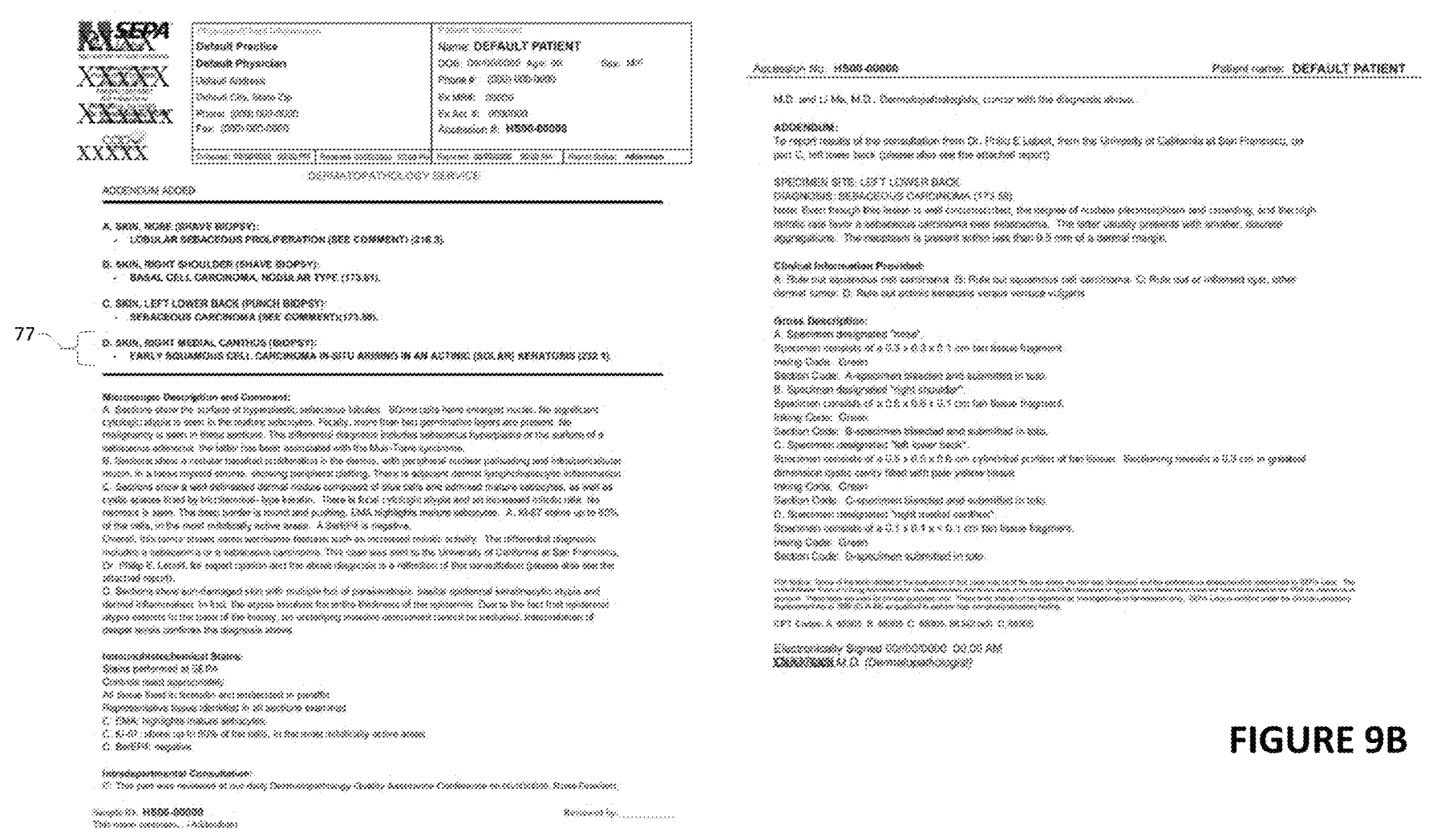

In some embodiments FIG. 9B, when a user "hovers" over the report (e.g., position mouse cursor or touch over display area of the report), future and/or past events pertaining to the event hovered over is shown. In this manner, it is ensured that the viewer is always looking at the event relative to other events associated with the same tracking number. For example, if the initial biopsy 73 and the genetic test 74 have already been completed when the viewer attempts to view the living PDF document 70, the information regarding them will already have been dynamically included in the living document 70. When the viewer, hovers over the display area of the genetic test report 74 in the document 70, future events 75 and 76 are displayed with a selection of information about each.

The living portable document file improves the efficiency of the care team by preventing "chart flipping" (i.e., where the care provider has to separately open and view multiple files to obtain the information regarding the full diagnosis and treatment associated with a particular pathology specimen) or having to search through the entire chart to see what happened.

Figure 9C:
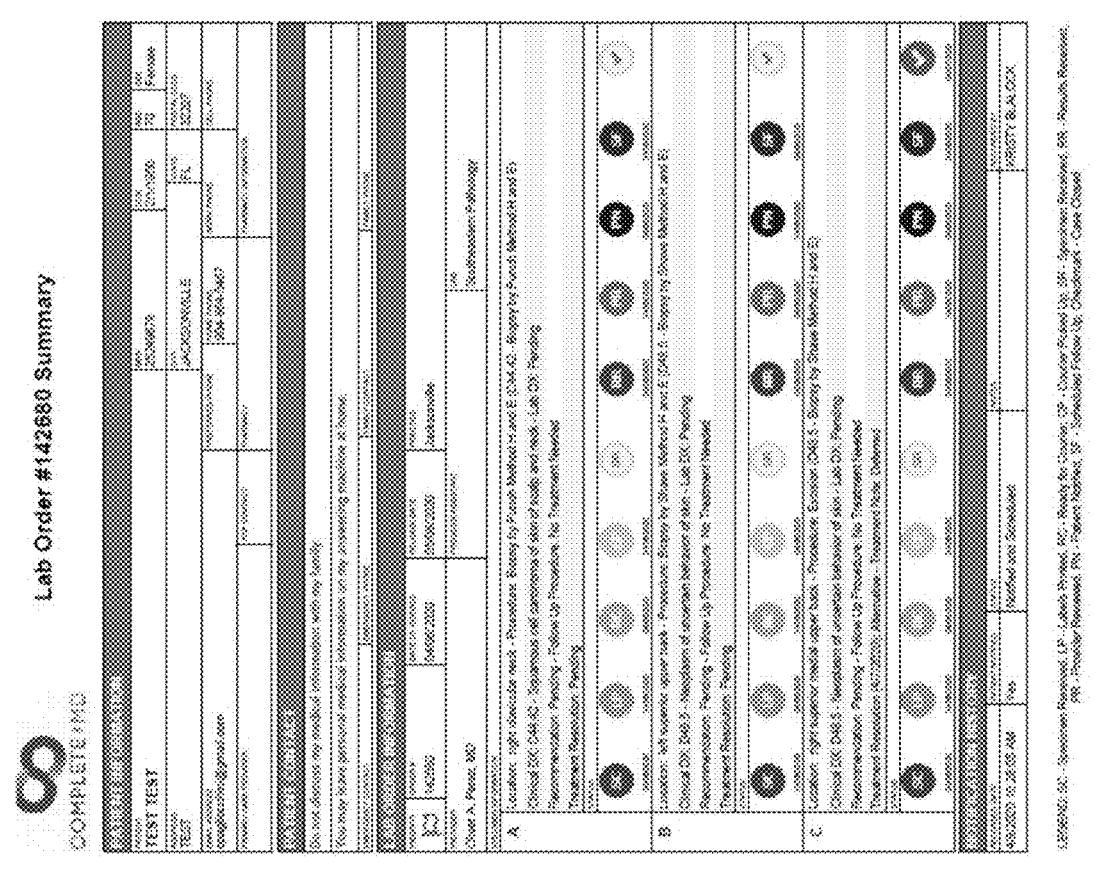

FIGS. 9B and 9C show other examples of living PDF documents, according to some embodiments. FIG. 9B shows an example dermatopathology report for a particular patient, having information about four separate biopsies (indicated as A, B, A and D) dynamically incorporated into the single document with the appropriate information from each biopsy and diagnosis being incorporated into the appropriate respective sections in the report. After having embedded the four tracking numbers for biopsies A, B, C and D in the report, the system 2 dynamically updates the report at runtime whenever the report is displayed and/or printed to include the information and results from the all the events completed so far in relation to each of the tracked events. In this manner a care provider or patient accessing a specified link to the document, is automatically served the most current information regarding each of the tracked events by the system traversing the tracked event and/or event chains for each of the tracked events embedded in the document accessed by the link.

FIG. 9C shows another example of a living PDF document in form of a lab order summary for a particular patient. Three tracked events (indicated as A, B and C) are embedded in the document, and for each of the tracked events, all events are shown with the current status (SC: Specimen Created, LP: Label Printed, RC: Ready for Courier, CP: Courier Pickup, CR: Courier Received, RR: Results Received, PR: Provider Review, PN: Patient Notified, SF: Scheduled Follow-up, TC: Treatment Completed). When the user hovers over the tracked event in a living portable document PDF, any future or past event associated with the tracked event or other event may be shown. Living PDF document data from the living PDF shown in FIG. 9C is shown at 77 in the living PDF shown in FIG. 9B.

The ability to show all information associated with a particular tracked event, including events directly linked to that tracked event and/or other tracked events that are linked to the particular tracked event, enables a care provider, patient or other authorized entity to view all of the information related to a particular set of tracked events regardless of the passing of time between events or the number of intervening events between two tracked or other events.

Figure 10:
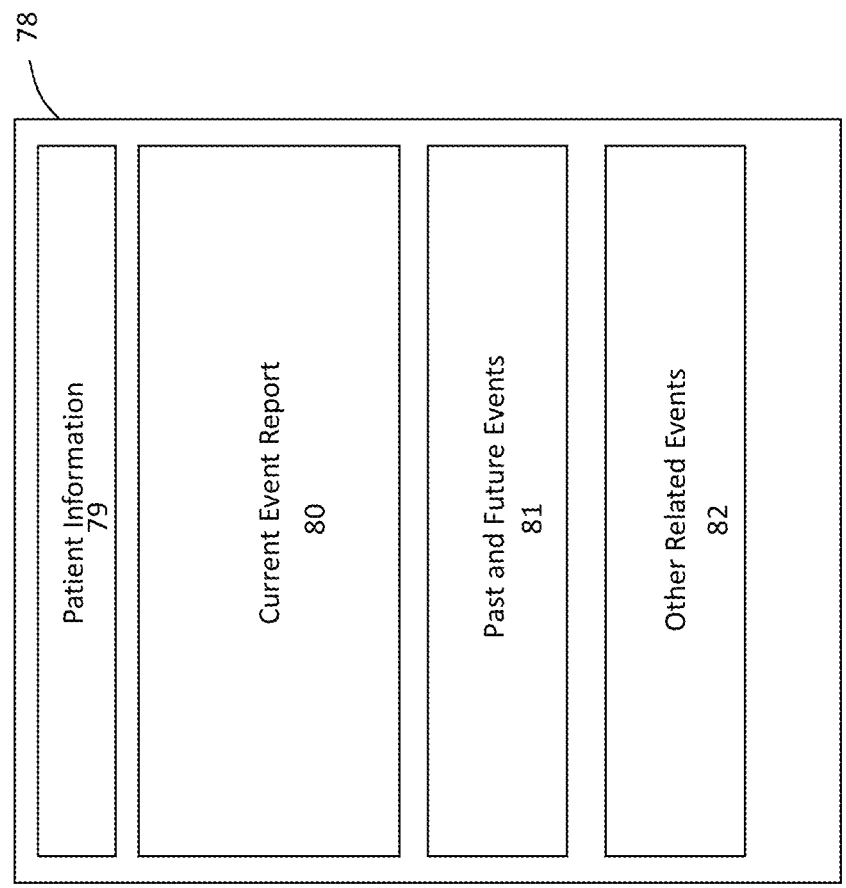
FIG. 10 schematically illustrates a display view, according to some embodiments.

FIG. 10 schematically illustrates a display view 78 that may be provided to the patient, medical professional and/or insurance professional, according to some embodiments. For example, the display view 78 may be rendered on a patient's mobile device 10, or a physician's display. The view may have separate areas for patient information (e.g. personally identifiable information, demographic information) 79, displaying details of a selected medical event 80, an area for displaying a scrollable list of medical events associated with the currently selected tracking number 81, and an area for displaying other associated tracking numbers or other medical events 82.

According to an embodiment, the display view 78 enables viewing the living PDF document described in relation to FIG. 9 above. For example, at a particular instant, the viewer may be viewing the details of the genetics test report 74 resulting from a tracked event corresponding one of the embedded tracking numbers. Then, the details of the genetics test report 74 is displayed in display area 80, and a scrollable list of past and future events associated with the report 74 (e.g. past event report 73 and future event reports 75 and 76) are indicated in display area 82.

Figure 11:
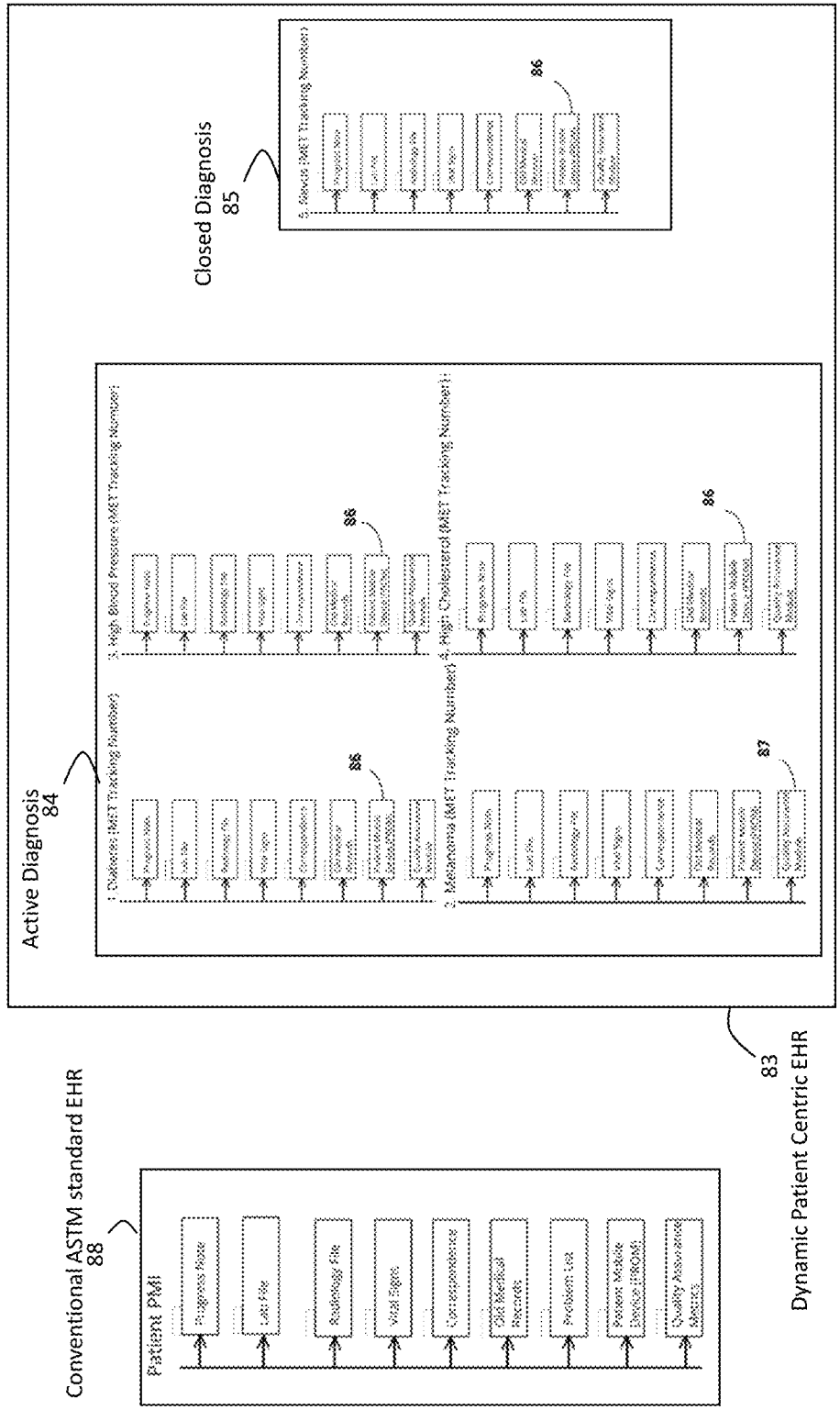
FIG. 11 schematically illustrates the difference between the Dynamic Patient-centric EHR according to some embodiments, and the Traditional ASTM Standard EHR.

FIG. 11 generally illustrates the basic data structure of the Dynamic Patient-Centric Medical Record (PCMR) according to an embodiment, compared to the ASTM Standard HL7 EHR. Medical record data in an ASTM standard EHR 88 is linked to a patient's PMI and filed in subfiles such as progress notes, lab files, imaging, correspondence, etc. The only shared link between files is the common patient PMI. In contrast the PCMR record 83 is indexed to MET tracking numbers such that linked data from any source is integrated into Diagnosis files and organized to optimize medical assessment. Linked data may be from labs, imaging centers, referral specialists, a patient's mobile device, or any linked source using the MET tracking number. The MET linked data creates an efficient, effective, economical, and productive patient care platform. Medical data is integrated efficiently as it requires no additional hardware. MET tracking effectively integrates data into the appropriate area for each care partner to use and eliminates staffing saving overhead cost. Having real-time linked data to assess each patient's ongoing diagnosis improves productivity enabling physicians to care for more patients with improved results than possible with current ASTM Standard EHRs.

FIG. 12 illustrates a flowchart for a process 90 for a living PDF in accordance with some example embodiments. Process 90 can be performed by a medical event tracking computer system 2 in a network 1. The medical event tracking system includes at least one memory, at least one network communication interface and a processing system having at least one processor. The at least one memory is configured to store a plurality of tracked medical event records, each tracked medical event record including a unique medical event tracking number and corresponding to a tracked medical event in relation to a patient. The process 90, comprising operations 91-94, is performed by the processing system.

At operation 91, the processing system obtains information associated with the patient from at least one electronic health record (EHR) system and at least one medical laboratory information (LIS) system via the at least one network communication interface. In some embodiments, the information associated with the patient may also be obtained from a PACS system. In example embodiments, the obtaining of the information may be performed by the QAM 6, in response to receiving an indication of a request to display the living PDF for the patient and/or a diagnosis associated with the patient. The information may be obtained via the APIs 7-9 from EHR system 3, LIS system 4 and PACS system 5. The information obtained by the QAM 6 may be stored in the memory as tracked medical event records associated with a unique medical event tracking number associated with the patient.

At operation 92, in response to a first request, the processing system displays information from one or more tracked medical event records stored in the at least one memory for the patient, the displayed information including information obtained from the at least one electronic health record system and the at least one medical laboratory information system. The first request may, for example, be a request received from a monitor and/or other computer connected to the QAM or a personal platform (e.g. mobile device 10) communicatively connected to the QAM. The QAM 6 may generate and transmit the information for display at a connected monitor/display and/or mobile device. The displayed information may include patient information obtained from the EHR, and diagnosis, test and/or imaging information from the EHR, PACS and/or the LIS. In some embodiments, the one or more tracked events for which the information is displayed includes separate diagnosis for the patient. In some embodiments, they include more than one event for the same diagnosis.

At operation 93, in response to a second request received in relation to the displayed information of a first tracked medical event record, identify, in the at least one memory and based on respective unique medical event tracking numbers included in corresponding records, a second one or more tracked medical events and a third one or more tracked medical events occurring before and after the event corresponding to the first tracked medical event record, respectively. The second request that is received at the QAM may be in response to a cursor hovering over the information displayed for the first tracked medical event. In response, based on the unique medical event tracking number of the first tracked medical event, the QAM identifies the set of second records for events occurring before the first tracked event and the set of third records for events occurring after the first tracked event. An example display is shown in FIG. 10.

At operation 94, the processing system dynamically displays information from one or more of the one or more second tracked medical events and/or the third tracked medical events. The events may be displayed in the available area dynamically being chosen for display in response to the movement of the cursor on the displayed information. In some embodiments, this can be facilitated by generating the display events within a hidden window behind a current display area, and exposing the generated events in accordance with movements of the cursor.

In some embodiments, the process 90 displays the plurality of sub-events comprising the medical diagnosis lifecycle associated with a tracked medical event for a diagnosis for the patient. Examples of lifecycle information are shown in FIGS. 9B-C.

Figure 13:
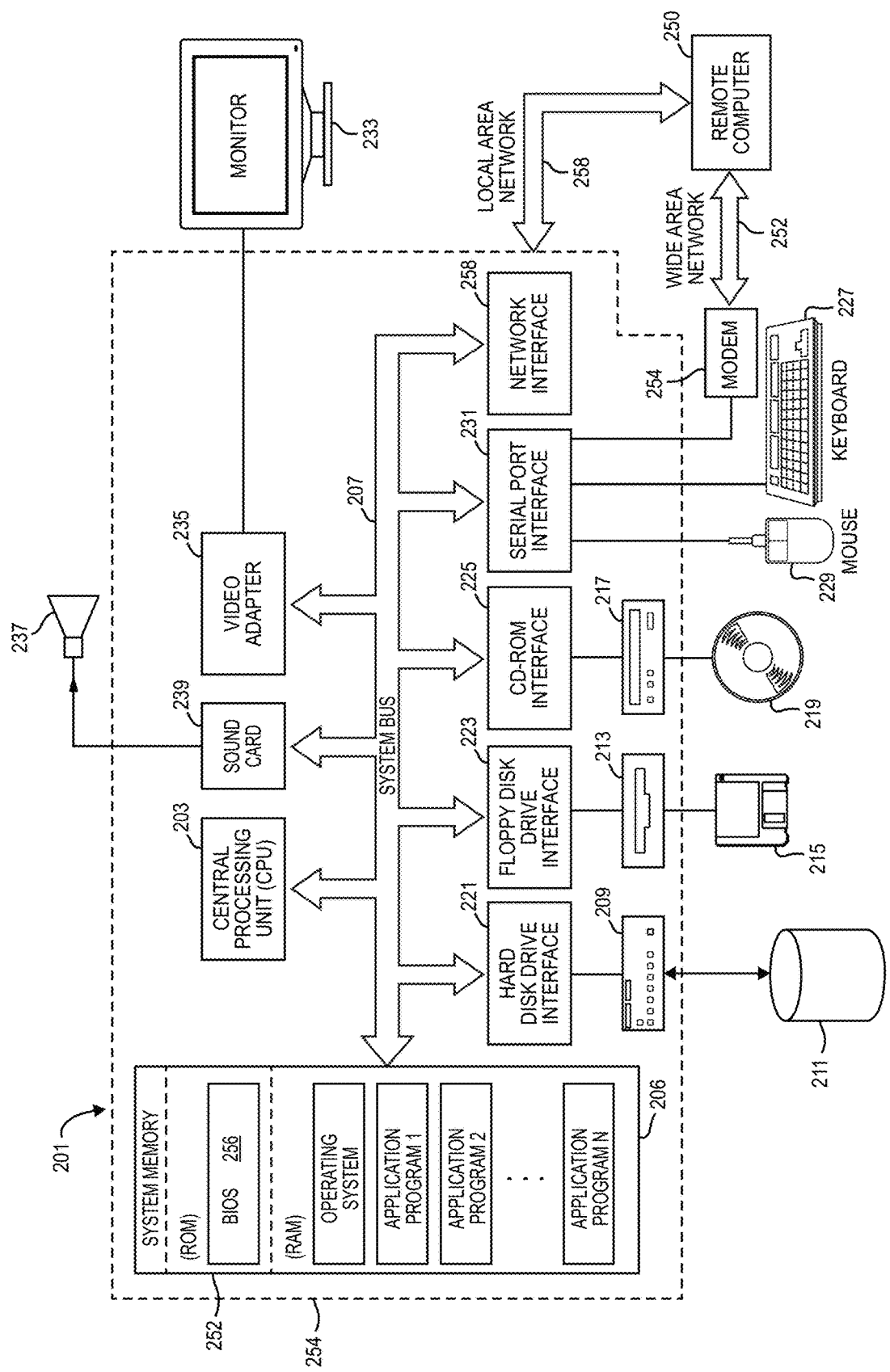
FIG. 13 is a schematic of a computer system, according to some embodiments.

FIG. 13 generally illustrates a computer system 201 suitable for use as the client and server components of the described system. It will be appreciated that the client and server computers will run appropriate software and that the client and server computers may be somewhat differently configured with respect to the processing power of their respective processors and with respect to the amount of memory used. Computer system 201 includes a processing system (e.g. one or more processors) 203 and a system memory 205. A system bus 207 couples various system components including system memory 205 to processing system 203. System bus 207 may be any of several types of bus structures including a memory bus or memory controller, a peripheral bus, and a local bus using any of a variety of bus architectures. System memory 205 includes read only memory (ROM) 252 and random-access memory (RAM) 254. A basic input/output system (BIOS) 256, containing the basic routines that help to transfer information between elements within computer system 201, such as during start-up, is stored in ROM 252. Computer system 201 further includes various drives and associated computer-readable media. A hard disk drive 209 reads from and writes to a (typically fixed) magnetic hard disk 211; a magnetic disk drive 213 reads from and writes to a removable "floppy" or other magnetic disk 215; and an optical disk drive 217 reads from and, in some configurations, writes to a removable optical disk 219 such as a CD ROM or other optical media. Hard disk drive 209, magnetic disk drive 213, and optical disk drive 217 are connected to system bus 207 by a hard disk drive interface 221, a magnetic disk drive interface 223, and an optical drive interface 225, respectively. The drives and their associated computer-readable media provide non-volatile storage of computer-readable instructions, SQL-based procedures, data structures, program modules, and other data for computer system 201. In other configurations, other types of computer-readable media that can store data that is accessible by a computer (e.g., magnetic cassettes, flash memory cards, digital video disks, Bernoulli cartridges, random access memories (RAMs), read only memories (ROMs) and the like) may also be used.

A number of program modules may be stored on the hard disk 211, removable magnetic disk 215, optical disk 219 and/or ROM 252 and/or RAM 254 of the system memory 205. Such program modules may include an operating system providing graphics and sound APIs, one or more application programs, other program modules, and program data. A user may enter commands and information into computer system 201 through input devices such as a keyboard 227 and a pointing device 229. Other input devices may include a microphone, joystick, game controller, satellite dish, scanner, or the like. These and other input devices are often connected to the processing unit 203 through a serial port interface 231 that is coupled to the system bus 207, but may be connected by other interfaces, such as a parallel port interface or a universal serial bus (USB). A monitor 233 or other type of display device is also connected to system bus 207 via an interface, such as a video adapter 235.

The computer system 201 may also include a modem or broadband or wireless adapter 237 or other means for establishing communications over the wide area network 239, such as the Internet. The modem 237, which may be internal or external, is connected to the system bus 207 via the serial port interface 231. A network interface 241 may also be provided for allowing the computer system 201 to communicate with a remote computing device 250 via a local area network 258 (or such communication may be via the wide area network 239 or other communications path such as dial-up or other communications means). The computer system 201 will typically include other peripheral output devices, such as printers and other standard peripheral devices.

As will be understood by those familiar with web-based forms and screens, users may make menu selections by pointing-and-clicking using a mouse, trackball or other pointing device, or by using the TAB and ENTER keys on a keyboard. For example, menu selections may be highlighted by positioning the cursor on the selections using a mouse or by using the TAB key. The mouse may be left-clicked to select the selection or the ENTER key may be pressed. Other selection mechanisms including voice-recognition systems, touch-sensitive screens, etc. may be used, and the invention is not limited in this respect.

The embodiments improve the performance of the present computerized diagnosis and treatment process by providing a quality assurance module that interfaces to EHR systems in the medical service providers and to lab information systems. In contrast to the tracking of medical events based on patient name or the like, the quality assurance module enables tracking patients based on respective medical events. The capability to track medical events enables the improving of the accuracy and completion of diagnostic and treatment plans. The quality assurance module, in some embodiments, integrates to EHR systems and lab information systems by well-defined API such that it enables the integration of numerous EHR systems and lab information systems. In some embodiments, the quality assurance module employs a two-level record structure to facilitate efficiently updating EHR systems etc., with the relevant tracked event information. The two-level records and associated data structures in some embodiments also facilitate the tracking of tracked events and other events in order to ensure the completion of diagnosis and treatment plans. In some embodiments the medical event tracking system is configured to send HL7 PDF data to traditional ASTM standard EMR systems, and includes the capability to link genetic and pharmacotheraphy information of a patient and/or treatment to one or more MET tracking numbers. As described above, in some embodiments, the medical event tracking system includes a platform to standardize MET tracking number closed loop quality time metrics communication, a platform for medical data life cycle standardization and dissemination, and/or a platform for patient centric medical records linked by MET tracking numbers. The medical event tracking system according to some embodiments provides for the creation of a competitive marketplace for medical quality defined by closed-loop documentation using MET tracking numbers.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

What is claimed is:

1. A medical event tracking computer system, comprising:
at least one memory configured to store a plurality of tracked medical event records, each tracked medical event record including a unique medical event tracking number and corresponding to a tracked medical event in relation to a patient;
at least one network communication interface; and
a processing system comprising at least one processor, the processing system being configured to:
provide, via the at least one network communication interface, a first application programming interface to at least one electronic health record system and a second application programming interface to at least one medical laboratory information system, wherein the first application programming interface and the second application programming interface are configured to convert between medical event codes encoded in one or more non-standard medical event coding schemes and medical event codes encoded in a standard medical event coding scheme;
obtain, using the at least one network communication interface, information associated with the patient from (1) the at least one electronic health record system via the first application programming interface and (2) the at least one medical laboratory information system via the at least one second application programming interface, convert, in the obtained information, medical event codes encoded in at least one of the one or more non-standard medical event coding schemes to corresponding medical event codes encoded in a standard medical event coding scheme, store the obtained information in tracked medical event records in the at least one memory, medical event codes in the tracked medical event records in the at least one memory being encoded in the standard medical event coding scheme and comprising the converted corresponding medical event codes, and associate at least one first timer with the at least one of the generated tracked medical event records, wherein an event type and/or event subtype and the associated first timer are set in accordance with a medical event code included in said obtained information associated with the patient from the at least one medical laboratory information system;
transmit, in response to said obtained information from one electronic health record system or medical laboratory information system of the at least one electronic health record system or the at least one medical laboratory information system and automatically in response to expiration of the at least one first timer, one or more alerts to users at a plurality of other electronic health record systems or medical laboratory information systems of the at least one electronic health record system or the at least one medical laboratory information system so that the users at the plurality of other electronic health record systems or medical laboratory information systems are informed in real-time of a current status of said at least one of the tracked medical event records;
display information from one or more tracked medical event records stored in the at least one memory for the patient, the displayed information including the obtained information;
identify, in the at least one memory and based on respective unique medical event tracking numbers included in corresponding records, a second one or more tracked medical events and a third one or more tracked medical events occurring before and after the event corresponding to said at least one tracked medical event record, respectively; and dynamically update the displayed information in real-time to include further information from one or more of said one or more second tracked medical events and/or said third tracked medical events.

2. The medical event tracking computer system according to claim 1, wherein the processing system is further configured to, for each tracked medical event for which information is displayed, display statuses of a plurality of stages of a corresponding medical diagnosis life cycle.

3. The medical event tracking computer system according to claim 1, wherein the processing system is further configured to:

obtain information for a new tracked medical event and an associated unique medical event tracking number;

identify, in the at least one memory, one or more other tracked medical events related to the new tracked medical event;

store a new tracked medical event record corresponding the new tracked medical event in the at least one memory and associate, based on corresponding unique medical event tracking numbers, the new tracked medical event record with records corresponding to the one or more other tracked medical events.

4. The medical event tracking computer system according to claim 1, wherein the processing system is further configured to:

provide an interface to receive information for one or more additional procedures, referrals, and/or outcomes for the patient in association with a tracked medical event for which a medical event tracking record is stored in the at least one memory; and provide an interface to define one or more parameters to evaluate a result of the one or more additional procedures, referrals, and/or outcomes.

5. The medical event tracking computer system according to claim 4, wherein the processing system is further configured to:

store, in the at least one memory, one or more records representing the received information of the one or more records corresponding to the one or more additional procedures, referrals, and/or outcomes;

configure one or more alerts in association with at least one of the one or more additional procedures, referrals, and/or outcomes; and responsive to a result associated with the one or more additional procedures, referrals, and/or outcomes, generate a message in accordance with the one or more alerts.

6. The medical event tracking computer system according to claim 5, wherein the result compared to a quality metrics associated with the one or more additional procedures, referrals, and/or outcomes.

7. The medical event tracking computer system according to claim 5, wherein the processing system is further configured to transmit the generated message to one or more of the at least one electronic health record system, the at least one medical laboratory information system, or a PACS system via the at least one network communication interface.

8. The medical event tracking computer system according to claim 1, wherein the second request is responsive to a cursor hovering over the displayed information for the first tracked medical event record.

9. The medical event tracking computer system according to claim 1, wherein the processing system is further configured to:

in response to receiving information corresponding to a particular tracked medical event, identify a plurality of other tracked medical events having a diagnosis corresponding to a diagnosis associated with the particular tracked medical event and for which corresponding tracked medical event records are stored in the at least one memory, wherein the plurality of other medical events are associated with one or more other patients;

identifying, by associating unique medical event tracking numbers associated with corresponding records stored in the at least one memory, one or more related tracked medical events associated with each of the plurality of other tracked medical events;

calculating statistics for the diagnosis associated with the particular tracked medical event, based on the identified one or more related tracked medical events; and display the calculated statistics.

10. The medical event tacking computer system according to claim 1, wherein the processing system is further configured to dynamically update a problem list associated with a diagnosis of the patient by dynamically associating in real-time, in the at least one memory, records corresponding to one or more subsequently-occurring tracked medical events with a record corresponding to the diagnosis of the patient based on medical event tracking numbers of the respective records.

11. The medical event tracking computer system according to claim 1, wherein the processing system is further configured to:

receive health-related measurements or reports from a portable platform associated with the patient; and automatically update one or more of the tracked medical event records stored in the at least one memory in accordance with the received health-related measurements or reports.

12. The medical event tracking computer system according to claim 11, wherein the processing system is further configured to control a wellness/medical device connected to the portable platform in accordance with a tracked medical event record stored in association with the patient, in the at least one memory.

13. The medical event tracking computer system according to claim 11, in response to the received health-related measurements or reports, determine whether one or more follow on medical events is necessary and for each one or more follow on medical events determined to be necessary: (1) generate a new event instance corresponding to the one or more follow on medical events in the at least one memory, (2) associate the new event instance with a unique medical event tracking number of a stored tracked medical event record associated with the patient, and (3) associate a timer with the new event instance.

14. The medical event tracking computer system according to claim 1, wherein the processing system is further configured to obtain said information associated with the patient from the at least one electronic health record system and/or the at least one medical laboratory information system by converting from a code in a message received from the at least one electronic health record system and/or the at least one medical laboratory information system to an event type and/or subtype stored in the at least one memory in association with a tracked medical event record.

15. The medical event tracking computer system according to claim 1, wherein the stored plurality of medical event records are devoid of personally-identifiable information of the patient.

16. The medical event tracking computer system according to claim 1, wherein the processing system is further configured to:
in response to a message received from the at least one electronic health record system, the at least one medical laboratory information system or a PACS, retro-actively update one or more stored patient information documents associated with a unique medical event tracking number associated with the patient.

17. A method performed by a processing system of medical event tracking processing system, comprising:
providing, via at least one network communication interface, a first application programming interface to at least one electronic health record system and a second application programming interface to at least one medical laboratory information system, wherein the first application programming interface and the second application programming interface are configured to convert between medical event codes encoded in one or more non-standard medical event coding schemes and medical event codes encoded in a standard medical event coding scheme;
obtaining, using the at least one network communication interface, information associated with a patient from (1) the at least one electronic health record system via the first application programming interface and (2) the at least one medical laboratory information system via the at least one second application programming interface, convert, in the obtained information, medical event codes encoded in at least one of the one or more non-standard medical event coding schemes to corresponding medical event codes encoded in a standard medical event coding scheme, and store the obtained information in tracked medical event records in at least one memory, medical event codes in the tracked medical event records in the at least one memory being encoded in the standard medical event coding scheme and comprising the converted corresponding medical event codes, and associating at least one first timer with the at least one of the generated tracked medical event records, wherein an event type and/or event subtype and the associated first timer are set in accordance with a medical event code included in said obtained information associated with the patient from the at least one medical laboratory information system;
transmitting, in response to said obtained information from one electronic health record system or medical laboratory information system of the at least one electronic health record system or the at least one medical laboratory information system and automatically in response to expiration of the at least one first timer, one or more alerts to users at a plurality of other electronic health record system or the at least one medical laboratory information system so that the users at the plurality of other electronic health record systems or medical laboratory information systems are informed in real-time of a current status of said at least one of the tracked medical event records;
displaying information from one or more tracked medical event records stored in the at least one memory for the patient, the displayed information including the obtained information;
identifying, in the at least one memory and based on respective unique medical event tracking numbers included in corresponding records, a second one or more tracked medical events and a third one or more tracked medical events occurring before and after the event corresponding to said at least one tracked medical event record, respectively; and
dynamically updating the displayed information in real-time to include further information from one or more of said one or more second tracked medical events and/or said third tracked medical events.

18. The method according to claim 17, further comprising, for each tracked medical event for which information is displayed, displaying statuses of a plurality of stages of a corresponding medical diagnosis life cycle.

19. A non-transitory computer readable storage medium storing instructions for medical event tracking, the instructions, when executed by a processing system including one or more processors, causes the processing system to perform operations comprising:
providing, via at least one network communication interface, a first application programming interface to at least one electronic health record system and a second application programming interface to at least one medical laboratory information system, wherein the first application programming interface and the second application programming interface are configured to convert between medical event codes encoded in one or more non-standard medical event coding schemes and medical event codes encoded in a standard medical event coding scheme;
obtaining, using the at least one network communication interface, information associated with a patient from (1) the at least one electronic health record system via the first application programming interface and (2) the at least one medical laboratory information system via the at least one second application programming interface, convert, in the obtained information, medical event codes encoded in at least one of the one or more non-standard medical event coding schemes to corresponding medical event codes encoded in a standard medical event coding scheme, and store the obtained information in tracked medical event records in at least one memory, medical event codes in the tracked medical event records in the at least one memory being encoded in the standard medical event coding scheme and comprising the converted corresponding medical event codes, and associating at least one first timer with the at least one of the generated tracked medical event records, wherein an event type and/or event subtype and the associated first timer are set in accordance with a medical event code included in said obtained information associated with the patient from the at least one medical laboratory information system;
transmitting, in response to said obtained information from one electronic health record system or medical laboratory information system of the at least one electronic health record system or the at least one medical laboratory information system and automatically in response to expiration of the at least one first timer, one or more alerts to users at a plurality of other electronic health record systems or medical laboratory information systems of the at least one electronic health record system or the at least one medical laboratory information system so that the users at the plurality of other electronic health record systems or medical laboratory information systems are informed in real-time of a current status of said at least one of the tracked medical event records;

displaying information from one or more tracked medical event records stored in the at least one memory for the patient, the displayed information including the obtained information;

identifying, in the at least one memory and based on respective unique medical event tracking numbers included in corresponding records, a second one or more tracked medical events and a third one or more tracked medical events occurring before and after the event corresponding to said at least one tracked medical event record, respectively; and dynamically updating the displayed information in real-time to include further information from one or more of said one or more second tracked medical events and/or said third tracked medical events.

20. The non-transitory computer readable medium according to claim 19, wherein the operations further comprise, for each tracked medical event for which information is displayed, displaying statuses of a plurality of stages of a corresponding medical diagnosis life cycle.

* * * * *